US008968793B2

(12) United States Patent
Hadar et al.

(10) Patent No.: US 8,968,793 B2
(45) Date of Patent: *Mar. 3, 2015

(54) ANTISEPTIC COMPOSITIONS AND USES THEREOF

(75) Inventors: Noa Hadar, Kibbutz Givat Brenner (IL); Amihay Freeman, Ben-Shemen (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 189 days.

This patent is subject to a terminal disclaimer.

(21) Appl. No.: 12/703,853

(22) Filed: Feb. 11, 2010

(65) Prior Publication Data

US 2010/0203158 A1 Aug. 12, 2010

Related U.S. Application Data

(60) Provisional application No. 61/151,539, filed on Feb. 11, 2009.

(51) Int. Cl.
| | | |
|---|---|---|
| *A01N 59/16* | (2006.01) | |
| *A01N 65/00* | (2009.01) | |
| *A01N 25/34* | (2006.01) | |
| *A61K 31/28* | (2006.01) | |
| *A61K 31/045* | (2006.01) | |
| *A61K 9/00* | (2006.01) | |
| *A61K 33/38* | (2006.01) | |
| *A61K 45/06* | (2006.01) | |

(52) U.S. Cl.
CPC .............. *A61K 31/045* (2013.01); *A61K 9/0014* (2013.01); *A61K 33/38* (2013.01); *A61K 45/06* (2013.01)
USPC ........... 424/618; 424/747; 424/402; 424/404; 514/495

(58) Field of Classification Search
USPC ........ 424/618, 49, 747, 402, 404, 78.24, 619; 514/184, 495
See application file for complete search history.

(56) References Cited

U.S. PATENT DOCUMENTS

| | | | |
|---|---|---|---|
| 5,562,643 A | 10/1996 | Johnson | |
| 5,607,683 A | 3/1997 | Capelli | |
| 5,643,589 A | 7/1997 | Chalmers | |
| 6,093,414 A | 7/2000 | Capelli | |
| 6,551,608 B2 | 4/2003 | Yao | |
| 7,364,565 B2 | 4/2008 | Freeman | |
| 2002/0041852 A1* | 4/2002 | Napolitano et al. | 424/49 |
| 2002/0137641 A1* | 9/2002 | Paul et al. | 510/130 |
| 2004/0166174 A1 | 8/2004 | Frank | |
| 2005/0058835 A1* | 3/2005 | Howdle et al. | 428/411.1 |
| 2005/0284803 A1* | 12/2005 | Dorward | 210/258 |
| 2006/0051385 A1 | 3/2006 | Scholz | |
| 2006/0105000 A1 | 5/2006 | Friedman | |
| 2006/0147533 A1* | 7/2006 | Balasubramanian et al. | 424/486 |
| 2006/0263445 A1* | 11/2006 | Frank | 424/618 |
| 2007/0106003 A1* | 5/2007 | Ho et al. | 524/440 |
| 2007/0225301 A1* | 9/2007 | Weidner | 514/259.41 |
| 2007/0255193 A1 | 11/2007 | Patel et al. | |
| 2008/0020061 A1 | 1/2008 | Hassler et al. | |
| 2008/0193559 A1 | 8/2008 | Kim | |
| 2010/0092578 A1 | 4/2010 | Fields et al. | |

FOREIGN PATENT DOCUMENTS

| | | |
|---|---|---|
| CN | 1480045 | 3/2004 |
| CN | 1676135 | 10/2005 |
| EP | 1839666 | 10/2007 |
| FR | 2972500 | 10/2000 |
| JP | 11-502539 | 3/1999 |
| JP | 2003-517463 | 5/2003 |
| JP | 2008-512389 | 4/2008 |
| WO | WO 97/25106 | 7/1997 |
| WO | WO 2007/077562 | 7/2007 |
| WO | WO 2008/027264 | 3/2008 |
| WO | WO 2008/033206 | 3/2008 |
| WO | WO 2008/069631 | 6/2008 |
| WO | WO 2008/069631 A1 * | 6/2008 |

OTHER PUBLICATIONS

Spacciapoli et al. ("Antimicrobial activity of silver nitrate against periodontal pathogens" in J. Periodontal Res. 2001, 36: 108-113).*
Morones et al. ("The bacterial effect of silver nanoparticles" in Nanotechnology 16 (2005), pp. 2346-2353).*
International Preliminary Report on Patentability Dated Aug. 25, 2011 From the International Bureau of WIPO Re. Application No. PCT/IL2010/000128.
Silver "Bacterial Silver Resistance: Molecular Biology and Uses and Misuses of Silver Compounds", FEMS Microbiology Reviews, 27:341-353, 2003.
International Search Report and the Written Opinion Dated May 6, 2010 From the International Searching Authority Re.: Application No. PCT/IL2010/000128.
Mariani et al. "Antimicrobial Activity of Commercial Grade Glycerine", Developments in Industrial Microbiology, XP002572766, 14: 356-360, Jan. 1, 1973. Abstract.
Spacciapoli et al. "Antimicrobial Activity of Silver Nitrate Against Periodontal Pathogens", Journal of Periodontal Research, XP002578901, 36(2): 108-113, Apr. 2001. Table 1.
Chopra "The Increasing Use of Silver-Based Products as Antimicrobial Agents: A Useful Development or a Cause for Concern", Journal of Antimicrobial Chemotherapy, 59: 587-590, 2007.
Cristani et al. "Interaction of Four Monoterpenes Contained in Essential Oils With Model Membranes: Implications for Their Antibacterial Activity", Journal of Agricultural and Food Chemistry, 55(15): 6300-6308, 2007.
Evrard "A New Colorimetric Assay for Studying and Rapid Screening of Membrane Penetration Enhancers", Pharmaceutical Research, 18(7): 943-949, 2001.
Klasen "A Historical Review of the Use of Silver in the Treatment of Burns. II. Renewed Interest for Silver", Burns, 26: 131-138, 2000.
Merck "Principles of Topical Dermatologic Therapy", The Merck Manual, Jun. 2009.
Patel "Menthol: A Refreshing Look at This Ancient Compound", Journal of the American Academy of Dermatology, 57(5): 873-878, Nov. 2007.
Schelz et al. "Antimicrobial and Antiplasmid Activities of Essential Oils", Fitoterapia, 77: 279-285, 2006.

(Continued)

*Primary Examiner* — Blessing M Fubara

(57) ABSTRACT

Antiseptic compositions and kits containing a source of silver ions and menthol, which act in synergy such that a concentration of silver ions in the composition is substantially reduced, are disclosed. Further disclosed are uses of the antiseptic compositions as disinfectants and in the treatment of wounds.

32 Claims, 4 Drawing Sheets

(4 of 4 Drawing Sheet(s) Filed in Color)

(56) References Cited

OTHER PUBLICATIONS

Trombetta et al. "Mechanisms of Antibacterial Action of Three Monoterpenes", Antimicrobial Agents and Chemotherapy, 49(6): 2474-2478, Jun. 2005.

Official Action Dated Mar. 26, 2012 From the US Patent and Trademark Office Re. U.S. Appl. No. 13/037,391.

Request for Examination Dated Jan. 23, 2014 From the ROSPATENT, Federal Government Institution, Federal Institute of Industrial Property of the Federal Service for intellectual Property, Patents and Trademarks of the Russian Federation Re. Application No. 2011137204 and its Translation into English.

Notice of Reason for Rejection Dated Jan. 31, 2014 From the Japanese Patent Office Re. Application No. 2011-548847 and Its Translation Into English.

Iscan et al. "Antimicrobial Screening of Mentha Piperita Essential Oils", Journal of Agricultural and Food Chemistry, 50(14): 3943-3946, 2002.

Kurita et al. "Synergistic Antimicrobial Effect of Acetic Acid, Sodium Chloride and Essential Oil Components", Agricultural and Biological Chemistry, 46(6): 1655-1660, 1982.

Osawa et al. "The Antibacterial Activities of Peppermint Oil and Green Tea Polyphenols, Alone and in Combination, Against Enterohemorrhagic *Escherichia coli*", Biocontrol Science, 4(1): 1-7, 1999.

Pattnaik et al. "Antibacterial and Antifungal Activity of Aromatic Constituents of Essential Oils", Microbios, 89(358): 39-46, 1997.

Office Action Dated Feb. 21, 2013 From the Israel Patent Office Re. Application No. 214558 and Its Translation Into English.

Official Action Dated Aug. 28, 2012 From the US Patent and Trademark Office Re. U.S. Appl. No. 13/037,391.

Translation of Notification of the Office Action Dated Jul. 31, 2012 From the State Intellectual Property Office of the People's Republic of China Re. Application No. 201080016122.X.

Official Action Dated May 27, 2014 From the US Patent and Trademark Office Re. U.S. Appl. No. 13/037,391.

Office Action Dated Jun. 30, 2014 From the Israel Patent Office Re. Application No. 214558 and Its Translation Into English.

WebMD "Colloidal Silver Overview Information", WebMD, Natural Medicine Comprehensive Database Consumer Version, Therapeutic Research Faculty, 2 P., 2009.

\* cited by examiner

ANTISEPTIC COMPOSITIONS AND USES THEREOF

RELATED APPLICATION

This application claims the benefit of priority from U.S. Provisional Patent Application No. 61/151,539 filed Feb. 11, 2009, the teachings of which are incorporated herein in their entirety.

FIELD AND BACKGROUND OF THE INVENTION

The present invention, in some embodiments thereof, relates to antiseptic compositions and uses thereof and, more particularly, but not exclusively, to antiseptic compositions which can be efficiently used in disinfecting surfaces such as bodily surfaces, and thus can be efficiently used, for example, in the treatment of infection-associated medical conditions such as acute and chronic wounds, burns, and surgical wounds.

Chronic wounds are characterized by an impaired healing process, a prolonged inflammatory stage, re-epithelization failure and defective extra-cellular matrix re-modeling. Cells accumulated within these wounds are senescent and their response to exogenous growth factors is reduced. The end result of the impaired healing process of the chronic wound is tissue breakdown, local necrosis and infection.

Management of wound bed is a multistep process necessary to achieve ultimate wound closure. Debridement, infection control, and wound closure are fundamental stages in the healing of chronic wounds.

In 2005, hospital acquired infections was ranked as the fourth-leading cause of death in the USA. It has been reported that approximately 10 million patients with traumatic wounds are treated in US emergency departments annually. Chronic wounds affect 1-3% of the entire population and include primarily venous leg ulcers, diabetic foot ulcers and pressure ulcers. Venous ulcers caused by chronic venous insufficiency are the most frequent (~70%) among the non-healing chronic wounds.

The number of emergency cases in which the infection of a chronic wound leads to life-threatening complications is increasing along with the growth in the number of chronic wounds infected with microorganisms resistant to antibiotics. The presence of bacterial colonization is one of the most crucial factors in the pathogenesis of most chronic wounds, resulting in high bacterial counts in wound tissue and in inflammatory host response.

In infected chronic wounds, wound healing is delayed or even abrogated when infected with heavy bacterial burden. The reduction of bacterial load is crucial and should be carried out prior to the healing process. In order to optimize the wound healing process, treatment of underlying factors such as malnutrition and ischemia along with decreasing bacterial load is often necessary.

Infection of chronic wounds delays healing and usually causes deterioration in the condition of the chronic wound bed, which can also result in complete breakdown of the wound. Apart from the detrimental effect on wounds, infection can cause systemic effect, which in some cases can be fatal.

Bacterial contamination delays wound healing through several different mechanisms e.g., persistent production of inflammatory mediators resulting in a prolonged inflammatory response that contributes to host injury and delays the healing process. In addition, bacteria compete with host cells for nutrients and oxygen essential for the wound healing process. Wound infection can also lead to tissue hypoxia, interrupt the development of granulation tissue, reduce the number of fibroblasts and collagen production and damage re-epithelization. Addressing the question of infected wound cleansing is therefore a major objective of wound care and plays a critical role in wound management.

A large fraction of foot ulcers results from complication of diabetes mellitus. These lesions frequently become infected and are often accompanied by osteomyelitis. Most infections in these lesions are mild to moderate in severity and can be managed with appropriate wound care and oral antibiotic therapy. Some infections, however, penetrate to the fascia, muscle, joint and bone. In theses cases, the patients require hospitalization, parenteral antibiotic therapy and surgical procedures. In some cases, foot infections in patients with diabetes can be difficult to treat and therapeutic failure often leads to a lower-extremity amputation. In addition, diabetic foot infections caused by methicillin-resistant *S. aureus* (MRSA) are associated with delayed healing an in many cases with amputations.

Antiseptic agents are commonly used to prevent and treat wound infections. Unlike antibiotics which act selectively on specific microorganisms, the antiseptic agents have multiple targets and a broader spectrum of activity. Most of the practiced antiseptic agents have not been shown to clearly impede healing.

Among the commercially available antiseptic agents the most commonly used in clinical practice are iodine, chlorhexidine, alcohol, acetate, hydrogen peroxide, boric acid, silver nitrate, silver sulfadiazine and sodium hypochlorite. Their efficacy, however, seems to be limited in view of recently reported outbreaks associated with contaminated antiseptics [Weber et al. 2007, *Antimicrob Agent Chemother* 51: 4217-4224].

Silver compounds have been widely used as wound antiseptics to counter bacterial infections in chronic and acute wounds including burns [Burrell 2003, *Ostomy Wound Manag* 49:19-24; Ovington 2004, *Ostomy Wound Manag* 50:1S-15]. Silver is known to block the growth of gram-negative and gram-positive bacteria. Ionic silver kills microorganisms but it is non-cytotoxic to proliferating granulation tissue. Silver formulations appear to increase the rate and degree of microbial killing, decrease exudate formation and recently reported to affect bacterial biofilms.

The most commonly used silver compounds are silver sulfadiazine (SSD) and silver nitrate ($AgNO_3$). Other commonly employed topical silver containing agents are nanocrystalline silver particles. Silver sulfadiazine (SSD) is usually used as a treatment for the prevention of infection in patients with burn wounds [Klasen 2000, *Burns* 26: 131-138]. Nanocrystalline silver releasing systems, e.g., Acticoat® [Tredget et al. 1998, *J. Burn Care Rehabil.* 19: 531-537] were developed in order to prolong its efficacy. Patients with infected chronic pressure ulcers were subjected to SSD and effective decreasing of the bacterial load were observed in all ulcers. SSD 1% cream significantly reduced venous ulcer, positively affecting wound cleansing and granulation tissue formation.

Silver nitrate was used first for the treatment of chronic wounds and ulcers [Klasen 2000, *Burns* 26: 131-138]. It was found to be effective against a wide range of bacterial flora especially against gram-negative bacteria. Nanocrystalline silver was incorporated later into wound dressings as a sustained release formulation for the treatment of acute and chronic wounds including burns [Voight et al. 2001, *Wounds*

13: B11-B21; Sondi and Salopek-Sondi 2004, *J Colloid Interf Sci* 275: 177-182; Parsons et al. 2005, *Wounds*, 17: 222-232].

Silver containing formulations for topical wound treatment are mostly based on silver containing wound dressing. The delivery and penetration of silver ions into the infected wound bed by such dressings is often limited by chemical reactions e.g. with chloride ions resulting in precipitation of inactive silver chloride, reducing the effective amount of antimicrobial silver ions reaching the targeted infected areas. Other drawbacks include silver affected coloration and local irritation.

In parallel with the common and excessive use of silver based topical treatments for wound management an increase in the number of reports on bacterial silver resistance was noticed [Silver 2003, *FEMS Microbiology Reviews* 27:341-353; Chopra 2007, *J Antimicrobial Chemotherapy* 59: 587-590].

Menthol is a natural monoterpene of plant origin, frequently used in dermatology as part of antipruritic, antiseptic, analgesic and/or cooling formulations. The molecular mechanisms underlying menthol contribution to these activities—and in particular to its antibacterial activity—were recently described [Patel, 2007, *J Am Acad Dermatol* 57: 873-878; Evrand 2001, *Pharma Resear* 18:943-949; Trombetta et al. 2005, *Antimicrob Agent Chemother* 49: 2474-2478; Schelz et al. 2006, *Fiterapia* 77: 279-285; Cristani et al. 2007, *J Agri Food Chem* 55: 6300-6308].

Hypertonic solutions are expected to add benefits to wound bed management by reduction of microbial load, enhanced exudate removal and impact on fluid circulation. Hypertonic saline solutions have been proven to be a very useful tool in neurosurgical practice.

Art of relevance include U.S. Pat. Nos. 5,643,589 and 5,562,643

Menthol has been described in the art as an antipruritic agent, antiseptic agent, analgesic and cooling agent, which can be used also in dermatological applications. Compositions comprising silver ions and menthol have also been described.

For example, The Merck Manual suggests combining menthol and silver in dermatological compositions in the chapter "Principles of Topical Dermatologic Therapy". Silver is defined as an antiseptic agent and menthol is defined as an anti-pruriritic agent (anti-itching agent) therein.

Additional relevant art include International Patent Application No. PCT/IL2007/000015, U.S. Pat. No. 6,551,608, U.S. patent application Ser. No. 11/783,668 (Publication No. 20070255193) and U.S. patent application Ser. No. 10/535,961 (Publication No. 20060105000), Antiseptic compositions comprising silver ions have also been disclosed in U.S. Pat. No. 5,607,683 and U.S. Pat. No. 6,093,414.

A continuous Streaming of Therapeutic solution (CST) is a new modality of chronic wound management developed by the present inventors, as well as others, and involves the continuous streaming of fresh doses of therapeutic solutions into the controlled wound environment. Streaming over chronic wounds allows for aseptic confinement of the wound, negative pressure therapy (pump-free), moist conditions, continuous cleansing and overall management of the wound bed. Such Continuous Streaming therapy has been disclosed, for example, in U.S. Pat. No. 7,364,565, to some of the present inventors.

SUMMARY OF THE INVENTION

In a search for an antiseptic composition with improved performance, the present inventors have surprisingly uncovered that a combination of silver ions and menthol exhibits a synergistic effect.

It has been further uncovered that this activity is retained in the presence of a hyperosmotic agent.

Thus, it is disclosed herein that silver ions-based antiseptic compositions exhibit a synergistic effect when combined with low concentration of menthol, in isotonic or hypertonic medium, wherein the silver ions are present at lower concentrations than are typically being used for antiseptic purposes. Such compositions are capable of exerting antimicrobial activity against a broad spectrum of pathogenic microorganisms while allowing pain relief, cooling and wound healing, without being associated with adverse side effects such as coloration and irritation, which are frequently observed for currently available silver ions-containing solutions.

It has further been demonstrated that antiseptic compositions comprising silver ions or complexes thereof at a concentration ranging from 0.005% w/v to 0.5% w/v in combination with menthol at a concentration ranging 0.05% w/v to 0.5% w/v and a hyperosmotic agent such as glycerol, are clear solutions devoid of precipitates.

Accordingly, acute and chronic wounds such as diabetic ulcers can be efficiently treated with the antiseptic compositions described herein. Moreover, higher rates of wound healing can be achieved when the antiseptic compositions described herein are applied over and through the wound in continuous flow so that the concentrations of the antimicrobial agent and the hyperosmotic agent in contact with the wound are kept constant.

It has further been demonstrated that such antiseptic compositions may act as preservatives, by preventing or reducing microbial growth in non-sterile conditions.

It has further been demonstrated that such antiseptic compositions exhibit effective fungicidal activity, which outperforms commercially available antifungal products. It has further been demonstrated that a combined, sequential treatment of an antiseptic composition as described herein and a polyhexadine-based commercial antiseptic product is highly effective in inhibiting growth of various fungal strains, particularly when the silver antiseptic composition is used first.

According to an aspect of some embodiments of the invention there is provided an antiseptic composition comprising, as active ingredients, menthol and a source of silver ions, and a pharmaceutically acceptable carrier, wherein a concentration of the silver ions in the composition is lower than 6 mM.

In some embodiments, the menthol and the silver ions act in synergy.

In some embodiments, a concentration of the menthol ranges from 0.3 mM to 32 mM.

In some embodiments, the concentration of the menthol ranges from 0.6 mM to 6.4 mM.

In some embodiments, a concentration of the silver ions ranges from 0.05 mM to 6 mM.

In some embodiments, a concentration of the silver ions ranges from 0.25 mM to 0.6 mM.

In some embodiments, a concentration of the silver ions ranges from 0.25 mM to 0.6 mM, and a concentration of the menthol ranges from 0.6 mM to 6.4 mM.

In some embodiments, a concentration of the silver ions is 0.29 mM, and a concentration of the menthol is 6.4 mM.

In some embodiments, a concentration of the silver ions is 0.29 mM, and a concentration of the menthol is 3.2 mM.

In some embodiments, a concentration of the silver ions is 0.29 mM, and a concentration of the menthol is 0.64 mM.

In some embodiments, a concentration of the silver ions is 0.44 mM, and a concentration of the menthol is 3.2 mM.

In some embodiments, a concentration of the silver ions is 0.6 mM, and a concentration of the menthol is 3.2 mM.

In some embodiments, a concentration of the silver ions is 0.6 mM, and a concentration of the menthol is 0.64 mM.

In some embodiments, the source of silver ions is selected from the group consisting of silver nitrate, silver sulfadiazine, an aminoalcohol-silver ion complex, an amino acid-silver ion complex and a polymer-silver ion complex.

In some embodiments, the polymer-silver ion complex is polyvinylpyrrolidone (PVP)-silver ion complex.

In some embodiments, the antiseptic composition further comprises a hyperosmotic agent.

In some embodiments, the hyperosmotic agent is selected from the group consisting of glycerol, polyethylene glycol, a polysaccharide, mannitol, and a combination thereof.

In some embodiments, the hyperosmotic agent is glycerol.

In some embodiments, a concentration of the glycerol ranges from 3% v/v to 15% v/v, based on the total volume of the antiseptic composition.

In some embodiments, a concentration of the glycerol is 10% v/v, based on the total volume of the antiseptic composition.

In some embodiments, the hyperosmotic agent is polyethylene glycol (PEG).

In some embodiments, a concentration of the PEG ranges from 8% v/v to 16% v/v based on the total volume of the antiseptic composition.

In some embodiments, the antiseptic composition is further comprising a solubilizing agent.

In some embodiments, the solubilizing agent is TWEEN 20.

In some embodiments, the pharmaceutically acceptable carrier is an aqueous solution.

In some embodiments, the antiseptic composition is formulated as a topical dosage form.

In some embodiments, the topical dosage form is selected from the group consisting of a cream, a spray, a gauze, a wipe, a sponge, non-woven fabrics, a cotton fabrics, a foam, a solution, a lotion, an ointment, a paste and a gel.

According to an aspect of embodiments of the invention there is provided an antiseptic kit comprising a packaging material and the antiseptic composition as described herein being packaged in the packaging material.

In some embodiments, the antiseptic kit is being identified in print, in or on the packaging material, for use in disinfecting a surface.

In some embodiments, the surface is a bodily surface.

In some embodiments, the antiseptic kit is identified in print, in or on the packaging material, for use in the treatment of a wound.

In some embodiments, the wound is selected from the group consisting of an acute wound, a chronic wound, a burn and a surgical wound.

In some embodiments, the chronic wound is selected from the group consisting of a diabetic ulcer, a venous ulcer and a pressure ulcer.

In some embodiments, at least one of the source of silver ions, the menthol and the pharmaceutically acceptable carrier is individually packaged within the packaging material.

In some embodiments, each of the source of silver ions, the menthol and the pharmaceutically acceptable carrier is individually packaged within the packaging material.

In some embodiments, the source of silver ions, the menthol and the pharmaceutically acceptable carrier are packaged together within the packaging material.

According to an aspect of embodiments of the invention there is provided a method of disinfecting a surface, the method comprising applying an effective amount of the antiseptic composition as described herein onto the surface, thereby disinfecting the surface.

In some embodiments, the surface is a bodily surface, the method being for disinfecting the bodily surface of a subject in need thereof.

In some embodiments, the method comprises topically applying the antiseptic composition onto the bodily surface.

In some embodiments, the bodily surface is a skin tissue.

In some embodiments, the method is being for treating an infection in said bodily surface.

In some embodiments, the infection is caused by a pathogenic microorganism selected from the group consisting of bacteria, yeast and fungi.

According to an aspect of embodiments of the invention there is provided a method of treating a wound, as described herein, in a subject in need thereof, the method comprising applying an effective amount of the antiseptic composition as described herein to the wound area, thereby treating the wound.

In some embodiments, the method comprises topically applying the antiseptic composition onto the wound area.

In some embodiments, topically applying the antiseptic composition is performed by streaming a flow of the antiseptic composition over and through the wound area.

In some embodiments, the flow is induced by gravity from at least one reservoir that comprises the antiseptic composition.

In some embodiments, the flow is induced by a pump being in fluid communication with at least one reservoir that comprises the antiseptic composition.

According to an aspect of some embodiments of the invention there is provided a use of the antiseptic composition described herein in the manufacture of a product for disinfecting a surface.

In some embodiments, the product is a medicament for disinfecting a bodily surface.

In some embodiments, the medicament is for treating an infection in said bodily surface.

In some embodiments, the infection is caused by a pathogenic microorganism selected from the group consisting of bacteria, yeast and fungi.

According to an aspect of some embodiments of the invention there is provided a use of the antiseptic composition described herein in the manufacture of a medicament for treating a wound, as described herein.

According to an aspect of some embodiments of the invention there is provided a process of preparing the antiseptic composition as described herein, the process comprising admixing the source of silver ions, the menthol and the pharmaceutically acceptable carrier, thereby obtaining the antiseptic composition.

In some embodiments, the method further comprises admixing a hyperosmotic agent with the composition.

In some embodiments, the method further comprises admixing a solubilizing agent with the composition.

In some embodiments, the solubilizing agent is admixed with the menthol, prior to admixing the menthol with the source of silver ions and the carrier.

In some embodiments, the solubilizing agent is TWEEN 20.

According to an aspect of some embodiments of the invention there is provided a method of reducing a concentration of silver ions in an antiseptic composition which comprises silver ions, the method comprising admixing with a source of the silver ions a synergistically effective amount of menthol, thereby reducing the concentration of the silver ions in the antiseptic composition.

In some embodiments, the concentration of the silver ions is reduced by at least 2-folds.

In some embodiments, the concentration of the silver ions is reduced by at least 10-folds.

According to an aspect of some embodiments of the invention there is provided a method of increasing an antiseptic activity of an antiseptic composition which comprises a source of silver ions at a concentration lower than 6 mM, the method comprising admixing with the composition a synergistically effective amount of menthol.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the images makes apparent to those skilled in the art how embodiments of the invention may be practiced.

In the drawings:

Figure 1:
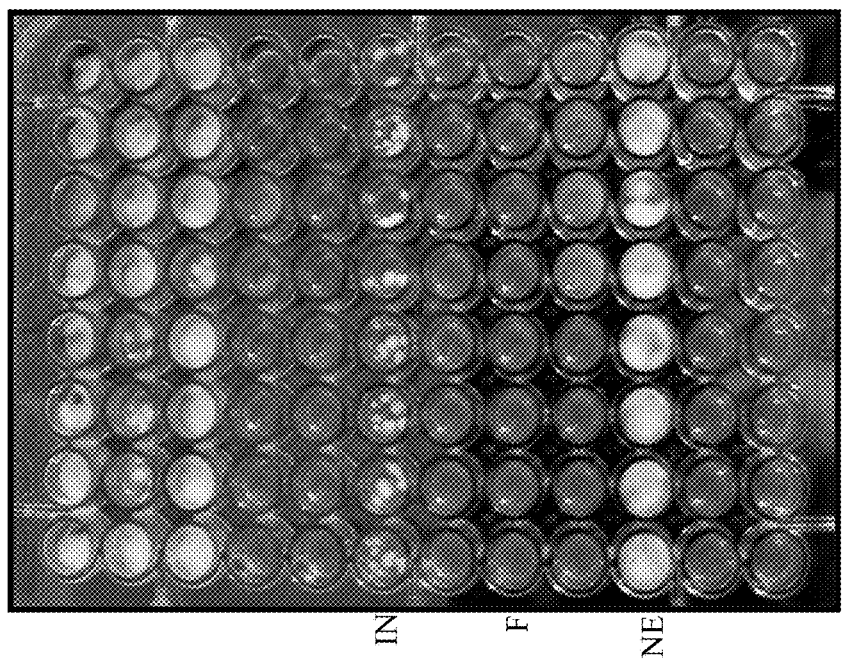

FIG. 1 presents an image generally illustrating the appearance of a fungal culture following 24 days incubation after 30 minutes exposure to a tested solution and subsequent washing, and presenting no growth (Fungicidal effect, denoted as "F"), minimal poor growth (Inhibitory effect, denoted as "IN") or full growth (No Effect, denoted "NE").

Figure 2:
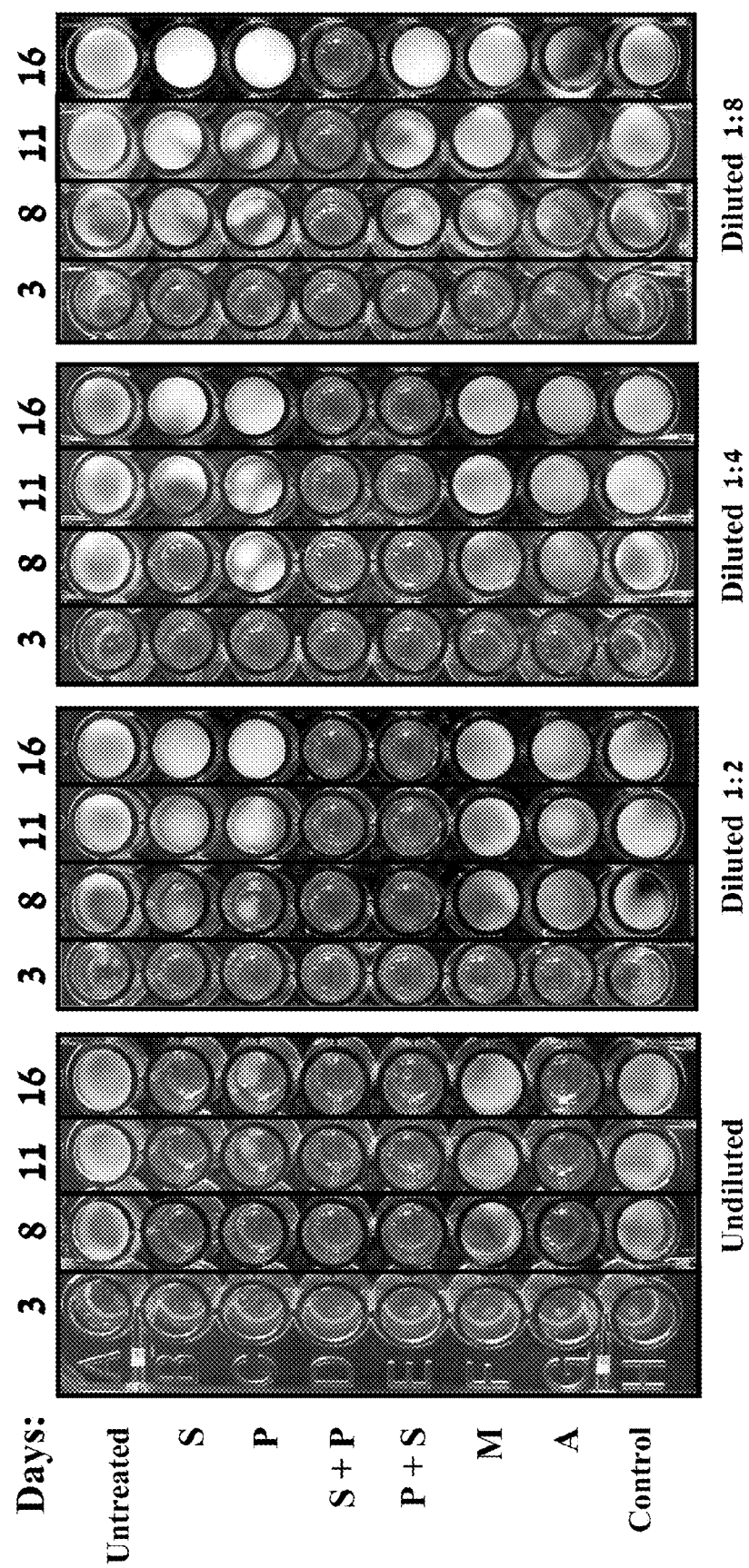
Figure 3:
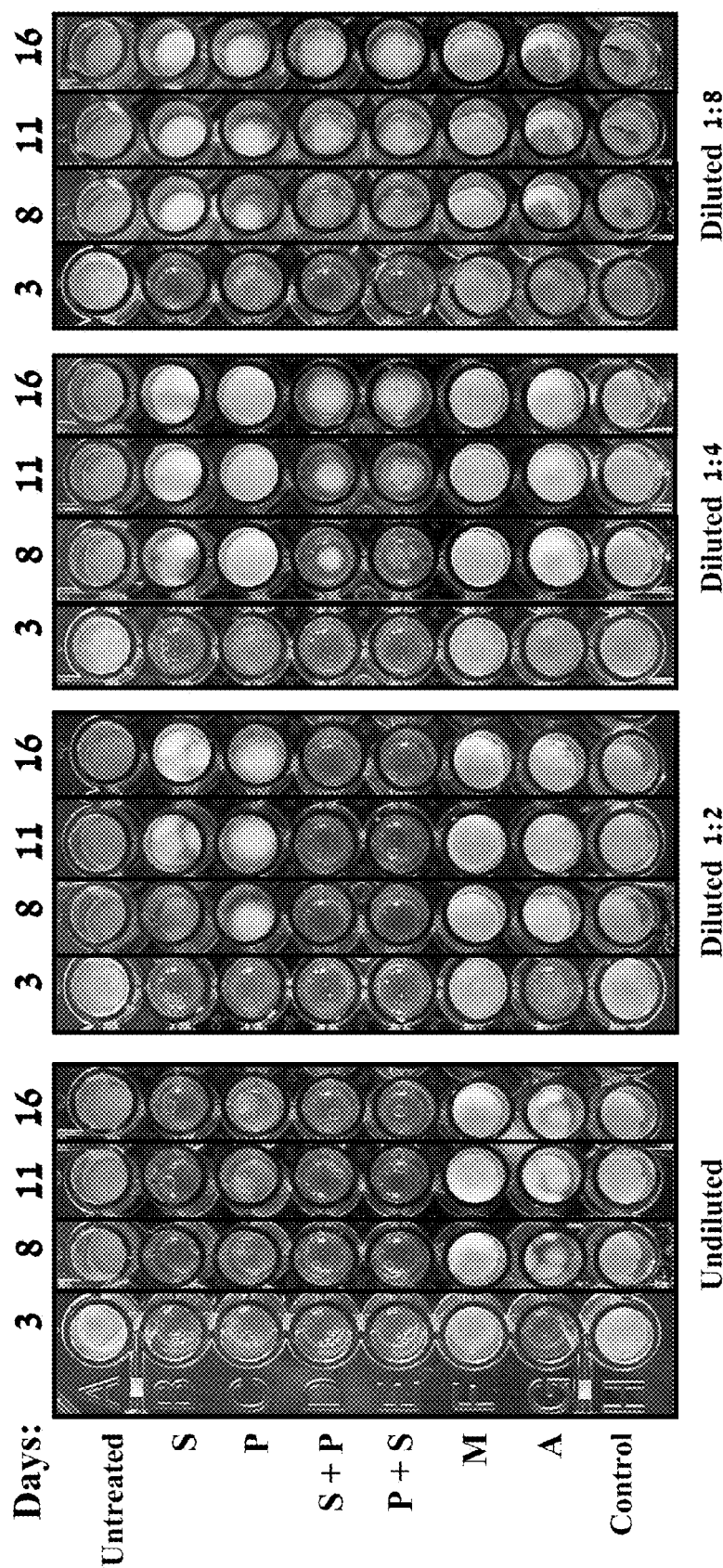
Figure 4:
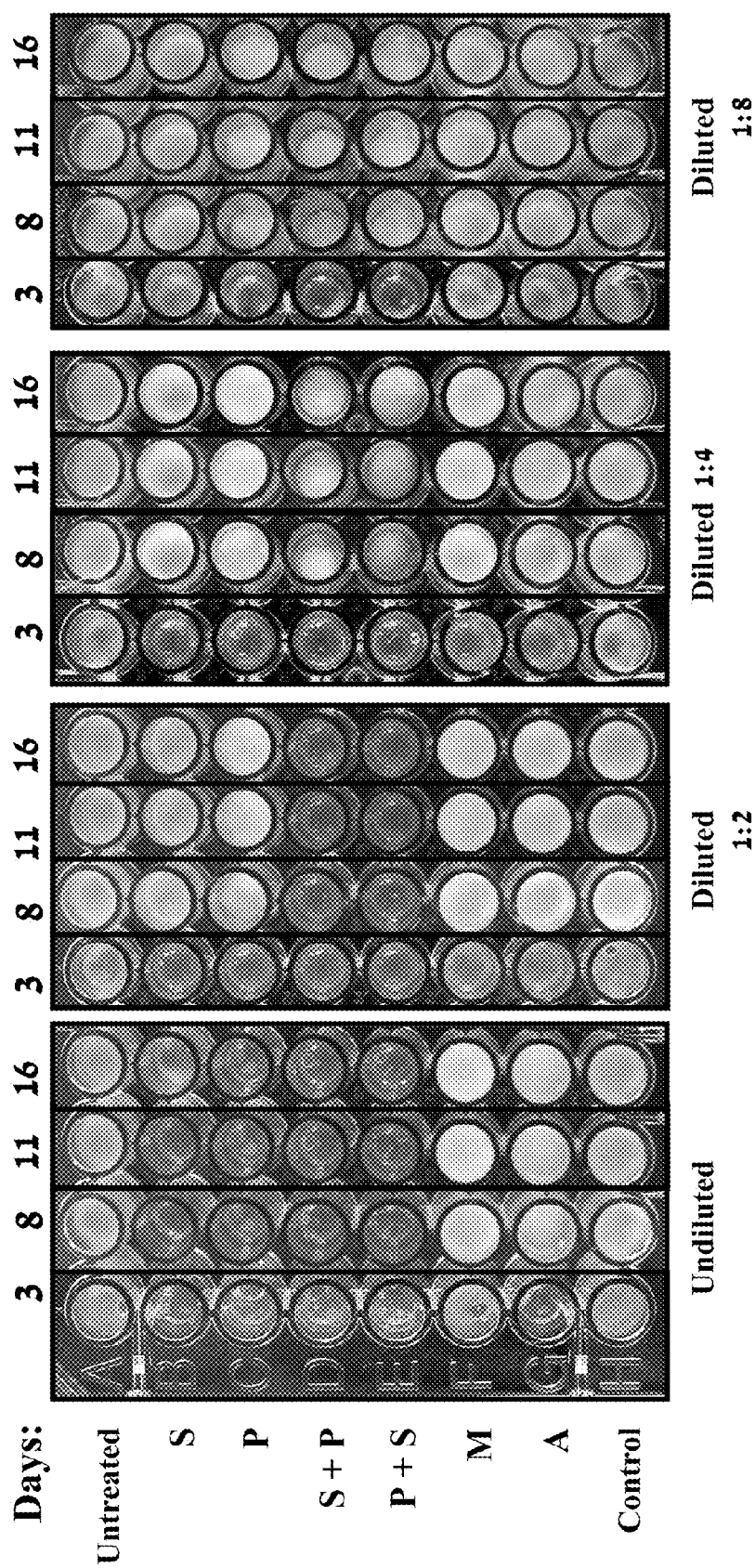

FIGS. 2, 3 and 4 present images illustrating the appearance of the exposed fungal culture, following 3, 8, 11 and 16 days incubation after 30 minutes exposure to each of the tested solutions and subsequent washing. Tested solutions included: a composition containing silver ions and menthol as described in Example 5 hereinabove (denoted "S"), PRONTOSAN® (denoted "P"), alternating subsequent exposures to a composition containing silver ions and menthol (S) and PRONTOSAN® (P), (denoted "S+P" and "P+S"), MICROCYN® (denoted "M") and ANACEPT® (denoted "A") and their dilutions (1:2; 1:4; 1:8). Tested fungal strains were a clinical strain of *Trichophyton rubrum* (FIG. 2); *Trichophyton rubrum* NCPF 118 commercial strain (FIG. 3); and a clinical strain of *Microsporum canis* (FIG. 4).

DESCRIPTION OF SPECIFIC EMBODIMENTS
OF THE INVENTION

The present invention, in some embodiments thereof, relates to antiseptic compositions and uses thereof and, more particularly, but not exclusively, to antiseptic compositions which can be efficiently used in disinfecting surfaces such as bodily surfaces, and thus can be efficiently used, for example, in the treatment of infection-associated medical conditions such as acute and chronic wounds, burns, and surgical wounds, and/or as preservatives.

The antiseptic compositions described herein comprise a source of silver ions and menthol, whereby the silver ions and the menthol act in synergy, thus allowing use of relatively low concentrations of each. The antiseptic compositions described herein are therefore readily prepared as solutions (as an example), with no precipitation of the active ingredients, and are devoid of the adverse side effects associated with currently available silver ions-based antiseptics while exhibiting high and broad therapeutic efficacy.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have recognized that one of the potential solutions to the development of microbial resistance to silver is the use of a combination of a source of silver ions, and another antibacterial agent which, together with the silver ions, exhibits an antibacterial (or antimicrobial) synergistic effect. Such a combination enables substantial reduction in silver input, and thus also eliminates side effects such as wound coloration and irritation caused by silver ions. Such a combination has, however, to be based on compatibility of all ingredients used with silver ions, so as to avoid potential precipitation of silver. Provided that suggested combinations are compatible, tests are readily available for feasibility demonstration of the synergistic antimicrobial effect (see, for example, Mackay et al. 2000 *Int J Antimicrob Agents* 15:125-129; and Peter et al. 2006, *J Antimic Chemother* 57: 573-576).

While many antibacterial, antimicrobial and/or antiseptic agents are known, it is difficult to predict which of these agents, when combined together, would act in synergy.

The term "antiseptic" as used herein describes the capability of an agent or a composition to effect reduction in microbial load, and/or to effect prevention of development of microbial load, by topical application of the agent or composition. An antiseptic composition or agent is thus capable of preventing or arresting the growth or action of microorganisms (such as, for example, bacteria, yeast and fungi) either by inhibiting their activity and/or growth or by destroying (killing) the microorganisms.

The term "antiseptic" is commonly used in the art to describe preparations for topical application to the infected living tissue or to any other infected surface, or a surface at risk of being infected, as is detailed hereinbelow.

Antiseptic compositions and agents are also referred to herein as antimicrobial compositions or agents. The term "antimicrobial", as used herein, describes a composition or agent capable of preventing or arresting the growth and/or action of microorganisms either by inhibiting the activity of the microorganisms, by inhibiting the growth of the microorganisms or by killing the microorganisms.

The terms "synergy", "synergism", and any grammatical diversion thereof, as used herein, describe a cooperative action encountered in combinations of two or more biologically active compounds in which the combined effect exhibited by the two compounds when used together exceeds the sum of the effect of each of the compounds when used alone. "Synergy" is therefore often determined when a value representing an effect of a combination of two active agents is greater than the sum of the same values obtained for each of these agents when acting alone.

A synergy between two antiseptic agents may be determined by methods well known in the art.

As presented in the Examples section that follows, it has been surprisingly uncovered that silver ions and menthol act in synergy. Synergy was determined by measuring the antiseptic activity of menthol alone and silver ions alone, against various bacteria, compared to their activity when administered together. The two agents are considered to act in synergy if the observed antiseptic activity of the agents, when administered together, is in excess of the cumulative antiseptic activity expected by combining the observed activity of the agents when administered alone.

In addition, synergy was demonstrated, and thus determined, when pharmacokinetic parameters of the antiseptic activity, exhibited when the agents are administered together, are superior to the same pharmacokinetic parameters of the antiseptic activity of the agents when each agent is administered alone. An exemplary pharmacokinetic parameter is the time length required for achieving a certain level of an antiseptic effect. Thus, the two agents are considered to act in synergy if the time length required for achieving this level of antiseptic effect is reduced when the agents are administered together, as compared to this time length when the agents are administered each alone.

It is noted in this regard that in pharmacokinetic parameters, usually there is no significance for the sum of values, and hence, any improvement in a pharmacokinetic parameter upon co-administration of two agents, relative to administration of each compound alone, is considered to reflect synergy.

Thus, it has been shown, for example, that synergistic antiseptic activity was observed for hyperosmotic solutions containing the silver ion source $AgNO_3$ and menthol at concentrations of 0.005% w/v %+0.1% w/v, 0.005% w/v+0.05% w/v, 0.005% w/v+0.01% w/v, 0.0075% w/v+0.05% w/v, 0.01% w/v+0.05% w/v and 0.01% w/v+0.01% w/v, respectively, when tested against *E. coli* ATCC47076 strain (see, Table 1 hereinbelow). These values correspond to a molar concentration for silver ions and menthol of 0.29 mM+6.4 mM, 0.29 mM+3.2 mM, 0.29 mM+0.64 mM, 0.44 mM+3.2 mM, 0.6 mM+3.2 mM and 0.6 mM+0.64 mM, respectively. Specifically, at these concentrations, the cumulative antiseptic activity of menthol and of silver ions when each administered alone was lower than the antiseptic activity observed when the agents were administered together.

It has been also shown that silver ions and menthol act in synergy against various types of bacteria, including *Klebsiella pneumoniae*, a Methicillin Resistant clinical strain of *Staphylococcus aureus* (MRSA), a clinical strain of *Staphylococcus epidermis*, a clinical strain of Extended Spectrum β-lactamase producing *Escherichia coli*, a clinical strain of Multi Drug Resistant *Acinetobacter baumannii*, and a clinical strain of Multi Drug Resistant *Pseudomonas aeruginosa* (see, Table 2 hereinbelow). In these studies, the synergistic effect of the silver ions and menthol was demonstrated by the shorter time length measured until a certain level of antiseptic activity was observed as compared to the time length until the same level of antiseptic activity was observed when each agent was administered alone.

It has been further shown that solutions containing silver ion source and menthol are clear solutions, devoid of precipitates.

It has further been demonstrated that the minimum inhibitory concentration of such a composition is obtained upon 1:4 dilution of the composition, and that the minimum bactericidal concentration of such a composition is obtained upon 1:2 dilution of the composition (see, Table 3 in the Examples section the follows).

Accordingly, an antiseptic composition as described herein can be beneficially used in any of the methods described herein, while being diluted by at least 1:2, and optionally by 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.5, 1:3.5, 1:3.6, 1:3.7, 1:3.8, 1:3.9, 1:4, and even upon higher dilutions (e.g., 1:5, 1:6, 1:7, 1:8, 1:9 and 1:10).

It has been further shown that upon 1:10 dilution, an exemplary composition comprising silver ions and menthol prevented growth of various bacterial and fungal strains in a non-sterile sample (see, Example 5 in the Examples section that follows).

The beneficial therapeutic effect of the antiseptic compositions described herein was further demonstrated in comparison with the commercially available products PRONTOSAN®, MICROCYN® and ANASEPT® (see, Example 6 in the Examples section that follows, and FIGS. 2-4). The antiseptic compositions described herein were shown to exhibit fungicidal activity against clinical fungal strains such as *Trichophyton rubrum* and *Microsporum canis*, which outperformed some of the commercially available products, and was found to be effectively combined with PRONTOSAN®.

The synergistic effect observed for the silver ions and menthol combination therefore enables to provide antiseptic compositions with reduced concentration of silver ions, along with taking advantage of other beneficial properties of menthol, such as, for example, its antipruritic effect, its coolant effect, etc.

These findings demonstrate that a composition comprising silver ions and menthol may serve as potent antiseptic composition, for disinfecting surfaces such bodily surfaces, and hence for the treatment or prevention of infection-associated conditions such as wounds, as detailed hereinunder.

These findings further demonstrate that a composition comprising silver ions and menthol may serve as potent antiseptic composition, for disinfecting surfaces of, for example, medical devices and storage containers, and for preventing development of microbial load on such surfaces.

Thus, according to an aspect of some embodiments of the invention there is provided an antiseptic composition comprising, as active ingredients, menthol and a source of silver ions, and a pharmaceutically acceptable carrier, wherein the concentration of the silver ions in the composition is lower than 6 mM.

According to some embodiments, the menthol and the silver ions act in synergy, as defined hereinabove.

Menthol, (5-methyl-2-propan-2-yl-cyclohexan-1-ol; CAS No. 89-78-1, MW=156 grams/mol) is a natural monoterpene of plant origin, frequently used in dermatology as part of antipruritic, antiseptic, analgesic and cooling formulations. Menthol is a waxy, crystalline substance, clear or white in color, which is solid at room temperature and melts slightly above it. Menthol has three asymmetric centers and exists as eight stereoisomers: (+)-menthol, (+)-isomenthol, (+)-neomenthol, (+)-neoisomenthol, (+)-menthol, (+)-isomenthol, (+)-neomenthol, (+)-neoisomenthol, all being encompassed by the term "menthol" as used herein.

The most common form of menthol occurring in nature is the (−)-menthol stereoisomer, which is assigned the (1R,2S, 5R) configuration and has the following structure:

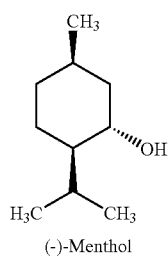

(-)-Menthol

The phrase "a source of silver ions", as used herein, describes a chemical moiety which generates silver ions when present in an appropriate medium. The silver ions can be generated once the compound is mixed with the carrier of the composition as described herein (as in the case of, for example, water-soluble silver salts in an aqueous carrier). Alternatively, the silver ions can be generated upon decomposition of a chemical complex that contains the silver ions, a decomposition that occurs once the complex is placed in the carrier of the composition. In such chemical complexes, the silver ions are typically engaged in coordinative interactions, while in silver salts, the silver ions are engaged in ionic interactions.

In some embodiments, the pharmaceutically acceptable carrier is an aqueous solution. In these embodiments, the source of silver ions is preferably a water-soluble silver salt such as, for example, silver nitrate, silver acetate and the partially water-soluble silver sulfadiazine.

Non-limiting examples of sources of silver ions that are suitable for use in the context of the present embodiments include silver nitrate, silver sulfadiazine, and silver ion complexes such as an aminoalcohol-silver ion complex, an amino acid-silver ion complex and a polymer-silver ion complex.

The phrase "aminoalcohol-silver ion complex" describes a complex of amino alcohol (i.e. a molecule which contains both an amine functional group and an alcohol functional group) with silver ions. Non-limiting examples of such complexes include aminoethanol, amino propyl alcohol, 2-amino-2-(hydroxymethyl)-1,3-propanediol, and aminobutyl alcohol.

In some embodiments, the concentration of the aminoalcohol component is about 50 mM.

The phrase "amino acid-silver ion complex" describes a complex of an amino acid (i.e., a molecule which contains both an amine functional group and a carboxylic acid functional group) with silver ions. In some embodiments, the amino acid is selected from the group of naturally occurring amino acids, non-natural amino acids and amino acid analogs. Non-limiting examples of such complexes include a histidine-silver(I) complex, a serine-silver complex and a lysine-silver complex.

The phrase "polymer-silver ion complex" describes a complex of a polymer with silver ions. The polymer in such a complex should have one or more functional groups (e.g., hydroxy, amine, oxo (=O), carboxylate, amide and the like) that coordinatively interact with the silver ions. The polymer may be synthetic, naturally-occurring or semi-synthetic polymer and is preferably biocompatible. Non-limiting examples of such polymer-silver ion complexes include polyvinylpyrrolidone (PVP)-silver ion complex, polyacrylamide-silver ion complex and polylysine-silver ion complex.

According to some embodiments, the polymer-silver ion complex is polyvinylpyrrolidone (PVP)-silver ion complex.

Polyvinylpyrrolidone is a water-soluble polymer with an excellent safety profile and a wide variety of applications in medicine, pharmacology, cosmetics and industrial production. Polyvinylpyrrolidone readily forms films and is used as a binder in many pharmaceutical tablets.

In some embodiments, where the silver ion source is a polyvinylpyrrolidone-silver ion complex, the polymer's concentration in the antiseptic composition ranges from 0.2% w/v to 10% w/v, based on the total volume of the antiseptic composition.

As used herein, "% w/v" describes a weight percentage of a component or an agent in the total volume of the composition. Thus, for example, 1% w/v describes 1 mg of a component or an agent in 100 ml of the composition.

The "% w/v" units, while expressing a mass present in a certain volume, can also be expressed as molarity, namely, moles per liter (M).

"% v/v" units describe a volume percentage of a component or an agent in the total volume of the composition.

As discussed hereinabove, the surprising findings that menthol and the silver ions act in synergy, allow utilizing an antiseptic composition that contains reduced concentrations of each agent, as compared to the concentration of each agent that is typically utilized for exerting an antiseptic activity, while still obtaining the desired antiseptic activity.

For example, silver nitrate-based antiseptic solutions at a concentration of 0.5% w/v are typically used to treat severe burns [Sweetman S C (ed) Martindale: The complete drug reference 35, London: Pharmaceutical press, 2007].

As further discussed hereinabove, such a concentration is relatively high and is associated with adverse effects such as wound coloration and irritation.

A concentration of 0.5% w/v silver nitrate corresponds to about 30 mM.

The concentration of menthol in currently known compositions for topical administration ranges between 0.25 w/v %, applied to the nasal mucous membrane for high fever and catarrh (a thick exudate of mucus) and up to 20% w/v for treatment of neuralgia, sciatica and lumbago.

The above concentration range of menthol corresponds to from about 15 mM to about 1.3 M.

It is noted herein that while the antiseptic properties of menthol are known, an indication of a recommended concentration of menthol in antiseptic composition could not be found in the art.

As exemplified in the Examples section that follows, silver nitrate solutions of concentrations lower than currently acceptable in antiseptic compositions (i.e., from 0.005% w/v to 0.01% w/v, corresponding to a range of from about 0.29 mM to about 0.6 mM) have limited antiseptic activity unless combined with menthol (see, Table 1). The addition of menthol, at a concentration of from 0.01 w/v % to 0.1 w/v %, corresponding to a concentration of from about 0.6 mM to about 6 mM, leads to a substantial enhancement of the antiseptic activity.

As further exemplified in the Examples section that follows, the limited antiseptic activity of silver nitrate solutions at the above-indicated lower concentrations is further demonstrated by the time length required for exhibiting a bactericidal activity (see, Table 2). The addition of low concentrations of menthol leads to substantial reduction of this time length.

Without being bound to any particular theory, it is hypothesized that the synergistic, antiseptic activity observed when silver ions are administered together with menthol results, in addition to the antiseptic activity exerted by menthol, also from the menthol ability to function as a penetration enhancer, which enhances the rate of penetration and the amount of silver ions penetrating into an infected area and/or microbial cells.

Thus, according to some embodiments of the invention, the concentration of the menthol in the antiseptic composition described herein ranges from about 0.3 mM to about 35 mM. This concentration range corresponds to a % w/v menthol concentration in a range of from 0.005% w/v to 0.5% w/v, based on the total volume of the antiseptic composition.

In some embodiments, the concentration of menthol ranges from about 0.6 mM to about 6.4 mM. This molar concentration range corresponds to a % w/v menthol concentration in a range of from 0.01% w/v to 0.1% w/v, based on the total volume of the antiseptic composition.

In some embodiments, the concentration of the source of silver ions is selected so as to provide a concentration of the silver ions in the composition which ranges from about 0.05 mM to about 6 mM.

Thus, in some embodiments the concentration of the source of silver ions is such that the concentration of silver ions in the composition is, for example, 0.05 mM, 0.06, mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 2.5 mM, 3 mM, 3.5 mM, 4 mM, 4.5 mM, 5 mM, 5.5 mM or 6 mM. Any other value of silver ions concentration between 0.05 mM and 6 mM is also contemplated.

In some embodiments, the silver ion source is $AgNO_3$ and the concentration of $AgNO_3$ ranges from 0.001% w/v to 0.5% w/v, based on the total volume of the antiseptic composition. In some embodiments, the concentration range of $AgNO_3$ is from 0.005% w/v to 0.01% w/v, based on the total volume of the antiseptic composition. In some embodiments, the concentration of the $AgNO_3$ ranges from 0.001% w/v to 0.5% w/v, and the concentration of the menthol ranges from 0.005% w/v to 0.5% w/v, based on the total volume of the antiseptic composition. In some embodiments, the concentration of the $AgNO_3$ ranges from 0.001% w/v to 0.5% w/v, and the concentration of the menthol ranges from 0.005% w/v to 0.5% w/v, based on the total volume of the antiseptic composition.

A concentration of the source of silver ions that provides such a concentration of silver ions can be readily determined based on the solubility and/or degree of decomposition of the source of silver ions in the selected carrier, its molecular weight and the number of silver ions that are generated from each molecule of the silver ion source.

In some embodiments, the concentration of the silver ions ranges from 0.29 mM to 0.6 mM.

The concentration of silver ions present in the antiseptic composition described herein can therefore be, for example, 0.06 mM (0.001% w/v $AgNO_3$), 0.29 mM (0.005% w/v $AgNO_3$), 0.6 mM (0.01% w/v $AgNO_3$), 2.9 mM (0.05% w/v $AgNO_3$) or 5.9 mM (0.1% w/v $AgNO_3$), all being substantially lower than the commonly used concentration of silver ions in currently available antiseptic compositions.

In some embodiments of the invention, the concentration of the silver ions ranges from 0.05 mM to 6 mM, and the concentration of the menthol ranges from 0.29 mM to 32 mM.

In some embodiments, the concentration of the silver ions ranges from 0.29 mM to 0.6 mM, and the concentration of the menthol ranges from 0.6 mM to 6.4 mM.

In one embodiment, the concentration of the silver ions is 0.29 mM, and the concentration of the menthol is 6.4 mM, In another embodiment, the concentration of the silver ions is 0.29 mM, and the concentration of the menthol is 3.2 mM.

In another embodiment, the concentration of the silver ions is 0.29 mM, and the concentration of the menthol is 0.64 mM.

In another embodiment, the concentration of the silver ions is 0.4 mM, and the concentration of the menthol is 3.2 mM.

In another embodiment, the concentration of the silver ions is 0.6 mM, and the concentration of the menthol is 3.2 mM.

In another embodiment, the concentration of the silver ions is 0.6 mM, and the concentration of the menthol is 0.64 mM.

In another embodiment, when the source of silver ions is $AgNO_3$, the concentration of the $AgNO_3$ is 0.01% w/v, and the concentration of the menthol is 0.05% w/v, based on the total volume of the antiseptic composition.

In another embodiment, the concentration of the $AgNO_3$ is 0.01% w/v, and the concentration of the menthol is 0.01% w/v, based on the total volume of the antiseptic composition.

In another embodiment, the concentration of the $AgNO_3$ is 0.0075% w/v, and the concentration of the menthol is 0.05% w/v, based on the total volume of the antiseptic composition.

In another embodiment, the concentration of the $AgNO_3$ is 0.005% w/v, and the concentration of the menthol is 0.1% w/v, based on the total volume of the antiseptic composition.

In another embodiment, the concentration of the $AgNO_3$ is 0.005% w/v, and the concentration of the menthol is 0.05% w/v, based on the total volume of the antiseptic composition.

In another embodiment, the concentration of the $AgNO_3$ is 0.005% w/v, and the concentration of the menthol is 0.01% w/v, based on the total volume of the antiseptic composition.

In some embodiments of the invention, the antiseptic composition described herein further comprises a hyperosmotic agent.

The phrase "hyperosmotic agent", as used herein, describes an agent which raises the osmotic pressure at a site where it is applied. A hyperosmotic agent is intended to increase the osmotic pressure around microorganisms such as bacteria, so as to kill or inhibit the growth of the microorganism. A composition which comprises a hyperosmotic agent has a higher osmotic pressure than isotonic fluid. Typically, such a composition has an osmotic pressure higher than a physiological pressure.

Exemplary hyperosmotic agents that are suitable for use in the context of embodiments of the invention include, but are not limited to, glycerol, polyethylene glycol (PEG), a polysaccharide, mannitol and any combination thereof.

In some embodiments, the hyperosmotic agent is compatible with the source of silver ions and the menthol, such that no precipitation is effected when it is present in the antiseptic composition.

Accordingly, a concentration of the hyperosmotic agent is selected compatible with their solubility in the pharmaceutically acceptable carrier utilized in the antiseptic composition, so as to provide a composition with an osmotic pressure that is higher than that of an isotonic solution.

In some embodiments, the hyperosmotic agent is biocompatible.

As used herein, the term "biocompatible" describes an agent or composition that is non-toxic and non-immunogenic when applied to a leaving organ, cell or tissue.

In some embodiments, the hyperosmotic agent is glycerol.

Glycerol is a chemical compound also commonly called glycerin. It is a colorless, odorless, viscous liquid and having low toxicity, which is widely used in pharmaceutical formulations.

Glycerol is preferably present within the antiseptic composition at a concentration of 3% v/v to 15% v/v, based on the total volume of the composition.

As used herein and in the art, a concentration unit of "% v/v" describes the volume percents of an agent or component of the total volume of the composition. Thus, for example, 1% v/v represents 1 ml of an agent or component in a 100 ml composition.

In some embodiments, the concentration of glycerol is 10% v/v.

In some embodiments, the hyperosmotic agent is polyethylene glycol (PEG).

PEG is a flexible, non-toxic (biocompatible), water-soluble polymer. PEGs are commercially available over a wide range of molecular weights, ranging from 300 DA to 10,000 KDa. Due to its characteristics, PEG can be used to create osmotic pressures.

Exemplary PEGs that are suitable for use in this context of the present embodiments include, but are not limited to, commercially available low molecular weight PEGs such as PEG 200 (Da), PEG 300 (Da) and PEG 400 (Da). PEG is preferably present within the antiseptic composition at a concentration of 8% to 16% v/v, based on the total volume of the composition.

As discussed hereinabove, it has been demonstrated that an antiseptic composition as described herein forms a clear solution, devoid of precipitates. Such compositions are advantageous since they can be readily applied on surfaces while utilizing any available technique for topical application.

In some cases, solubilizing agents, or any other agents, are added to the composition in order to facilitate the complete dissolution of its components.

Thus, according to some embodiments of the invention, the composition further comprises a solubilizing agent.

The term "solubilizing agent", as used herein and in the art, describes a chemical agent which is capable of facilitating the dissolution of insoluble or poorly soluble components in a solution containing same.

A solubilizing agent, according to some embodiments of the invention, should be compatible with the source of silver ions used, so as to avoid precipitation of non-soluble silver salts.

It is noted herein that most of the silver salts are insoluble or have limited solubility in aqueous solutions, and hence any component that is added to the antiseptic composition described herein should be considered by its effect on the silver solubility in the composition, in order to maintain an effective concentration of soluble silver ions in the composition.

Representative examples of solubilizing agents that are usable in the context of the present invention include, without limitation, complex-forming solubilizers such as cyclodextrin, polyvinylpyrrolidone, and micelle-forming solubilizers such as TWEENS and spans, e.g., TWEEN 80 and TWEEN 20. Other solubilizing agents that are usable in the context of embodiments of the invention include, for example, polyoxyethylene sorbitan fatty acid ester, polyoxyethylene n-alkyl ethers, n-alkyl amine n-oxides, poloxamers, organic solvents, phospholipids and cyclodextrines.

The selection of the solubilizing agent is based on its being compatible with silver ions without causing precipitation of silver in the selected carrier.

As described in the Examples section that follows, menthol is used in the composition described herein in combination with an appropriate solubilizing agent, such as TWEEN 20 and the like. The solubilizing agent facilitates the formation of a stable and clear solution containing the silver ion source and the menthol.

Thus, in some embodiments, the solubilizing agent is TWEEN 20. According to some embodiments, the ratio between the menthol and TWEEN 20 is 1:10, e.g., 0.05% w/v menthol and 0.5% w/v TWEEN 20.

Without being bound to any particular theory, it is suggested that the addition of TWEEN 20 to the antiseptic composition described herein may further provide for enhanced activity of the composition due to the penetration enhancing properties of TWEEN 20. Thus, it may be suggested that silver ions, menthol and TWEEN 20, all act in synergy, thus further allowing to beneficially utilize low concentrations of silver ions in the antiseptic composition while exhibiting the desired activity.

The antiseptic composition described herein can further comprise additional ingredients, which are aimed at improving or facilitating its preparation, application and/or performance. Such additional ingredients include, for example, anti-irritants, anti-foaming agents, humectants, deodorants, antiperspirants, pH adjusting agents, preservatives, emulsifiers, occlusive agents, emollients, thickeners, penetration enhancers, colorants, propellants (depending on the final form of the composition) and surfactants.

Representative examples of humectants that are usable in this context of the present invention include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

Suitable pH adjusting agents include, for example, trisimidazole trimethylamine buffers, and any other buffer solutions compatible with the other components without causing precipitation of any of the components.

Representative examples of deodorant agents that are usable in the context of the present embodiments include, without limitation, 2,4,4'-trichloro-2'-hydroxy diphenyl ether, and diaminoalkyl amides such as L-lysine hexadecyl amide.

Suitable preservatives that can be used in the context of the present embodiments include, without limitation, one or more alkanols, parabens such as methylparaben and propylparaben, propylene glycols, sorbates, urea derivatives such as diazolindinyl urea, or any combinations thereof.

Suitable emulsifiers that can be used in the context of the present embodiments include, for example, one or more sorbitans, alkoxylated fatty alcohols, alkylpolyglycosides, soaps, alkyl sulfates, or any combinations thereof.

Suitable occlusive agents that can be used in the context of the present embodiments include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients, that can be used in the context of the present embodiments include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners that can be used in the context of the present embodiments include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, and mixtures thereof.

Suitable penetration enhancers usable in context of the present embodiments include, but are not limited to, polyethylene glycol monolaurate (PEGML), propylene glycol (PG), propylene glycol monolaurate (PGML), glycerol monolaurate (GML), lecithin, the 1-substituted azacycloheptan-2-one s, particularly 1-n-dodecylcyclazacycloheptan-2-one (available under the trademark Azone® from Whitby Research Incorporated, Richmond, Va.), alcohols, menthol, TWEENS such as TWEEN 20, and the like. The permeation enhancer may also be a vegetable oil. Such oils include, for example, safflower oil, cottonseed oil and corn oil.

Suitable anti-irritants that can be used in the context of the present embodiments include, for example, steroidal and non steroidal anti-inflammatory agents or other materials such as menthol, aloe vera, chamomile, alpha-bisabolol, cola nitida extract, green tea extract, tea tree oil, licoric extract, allantoin, caffeine or other xanthines, glycyrrhizic acid and its derivatives.

Any of the additional ingredients or agents described herein is preferably selected as being compatible with the silver ions, at least within the concentration range it is used within the composition, such that no precipitation occurs and there is no interference with the availability of the silver ions in the composition.

Any of the additional ingredients described herein is further preferably selected as being biocompatible.

It is noted that some agents or ingredients included within the composition may provide a dual effect. For example, menthol is used to act in synergy with silver ions for enhancing an antiseptic activity, but is also useful as a penetration enhancer and as an anti-irritant. TWEEN 20 can be used as a solubilizing agent but is also known to act as a penetration enhancer.

In some embodiments, the antiseptic composition further comprises an additional therapeutically active agent, for example, an agent capable of treating the indicated condition, as detailed herein, or an agent capable of disinfecting a surface, as is further detailed hereinbelow (e.g., a bodily surface). In some embodiments, the antiseptic composition further comprises an agent capable of preventing, reducing or inhibiting a growth of a disinfecting microorganism e.g. bacteria or fungi, or an agent capable of reducing a load of a disinfecting microorganism.

In some embodiments, the antiseptic composition further comprises an additional agent that is capable of treating a wound, as described herein. Exemplary additional therapeutically active agents include, but are not limited to, betaine and polyhexadine.

The antiseptic composition described herein is formulated together with a pharmaceutically acceptable and suitable carrier.

As used herein, the term "pharmaceutically acceptable carrier" describes a carrier or a diluent that is used to facilitate the administration of the composition and which does not cause significant irritation to an organism and does not abrogate the biological activity and properties of the administered active compounds. Examples, without limitations, of carriers include water, buffered aqueous solutions, propylene glycol, emulsions and mixtures of organic solvents with water, as well as solid e.g. powdered) and gaseous carriers.

Techniques for formulation and administration of drugs may be found in "Remington's Pharmaceutical Sciences" Mack Publishing Co., Easton, Pa., latest edition, which is incorporated herein by reference.

Antiseptic compositions for use in accordance with the present embodiments thus may be formulated in conventional manner using one or more pharmaceutically acceptable carriers, excipients and/or auxiliaries, which facilitate processing of the compounds into preparations which can be used pharmaceutically. The dosage may vary depending upon the dosage form employed and the route of administration utilized.

The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutically acceptable carrier can be either an organic carrier or an aqueous carrier. In some embodiments, the carrier is an aqueous carrier, in which the source of silver ions is soluble. In some embodiments, the aqueous carrier is a buffer solution.

An aqueous carrier preferably comprises injectable-grade water, i.e., USP grade "water for injection". However, other forms of purified water may be suitable, such as, for example, distilled and deionized water.

Aqueous formulations are preferred since these formulations are gentle to both skin and mucosal tissue and are suitable for use on open wounds. However, non-aqueous formulations are also contemplated. For example, in cases where the antiseptic composition is in a form of a paste or an emulsion, non-aqueous carriers or mixed carriers of aqueous and organic carriers can be used, as long as silver ions are generated in the carrier.

The antiseptic composition may be formulated for administration in either one or more of routes, depending on the area to be treated.

According to some embodiments, the antiseptic composition is formulated for topical application, as a topical dosage form.

As used herein, the phrase "topical dosage form" describes a dosage form suitable for topical administration to the treated area.

By selecting the appropriate carrier and optionally other ingredients that can be included in the composition, the antiseptic compositions described herein may be formulated into any form normally employed for topical application. Hence, the compositions described herein can be, for example, in a form of a cream, an ointment, a paste, a gel, a lotion, a milk, a solution, an aerosol, a spray, a foam, a gauze, a wipe, a sponge, a non-woven fabric, a cotton fabric, a pledget, a patch and a pad.

Exemplary topical dosage forms include, but are not limited to, a cream, a spray, a gauze, a wipe, a sponge, non-woven fabrics, a cotton fabrics, a foam, a solution, a lotion, an ointment, a paste and a gel.

Such topical dosage forms may optionally further comprise an adhesive, for facilitating the topical application of the composition onto the treated area for a prolonged time period.

In some embodiments, the antiseptic composition is formulated as a liquid reservoir, to be applied as drops, spray, aerosol, liquid, foam and the like. Suitable carriers and other ingredients are used in these cases. For example, for application as an aerosol or foam, a propellant is used.

In some embodiments, the antiseptic composition is formulated as a cream.

An exemplary cream formulation can be obtained by mixing the antiseptic composition described herein with a carrier comprising cellulose derivatives such as cellulose acetate, hydroxyethyl cellulose and/or a polyethylene glycol.

The amount of a composition to be administered will be, of course, dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may comprise, for example, glass or plastic foil. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions of the invention formulated in a compatible pharmaceutical carrier may also be prepared, placed in an appropriate container, and labeled for disinfection purposes or for treatment of wounds, as detailed herein.

The compositions described herein may be packed or presented in any convenient way. For example, they may be packed in a tube, a bottle, a dispenser, a squeezable container, or a pressurized container, using techniques well known to those skilled in the art and as set forth in reference works such as Remington's Pharmaceutical Science 15$^{th}$ Ed. It is preferred that the packaging is done in such a way so as to minimize contact of the unused compositions with the environment, in order to minimize contamination of the compositions before and after the container is opened.

The compositions described herein are preferably supplied in the concentration intended for use but may also be prepared as concentrates that are diluted prior to use. For example, concentrates requiring dilution ratios of 2:1 to 10:1 parts carrier (e.g., water) to concentrate are contemplated. The higher limit of the concentrate is limited by the solubility and compatibility of the various components at higher concentrations.

In some embodiments, the antiseptic composition described herein is packaged in a packaging material and identified in print, in or on the packaging material, for use in disinfecting a surface, as described herein.

In some embodiments, the antiseptic composition described herein is packaged in a packaging material and identified in print, in or on the packaging material, for use in disinfecting a bodily surface, as is further detailed hereinbelow.

In some embodiments, the antiseptic composition is packaged in a packaging material and identified in print, in or on the packaging material, for use in the treatment of wounds.

In some embodiments, the antiseptic composition is packaged in a packaging material and identified in print, in or on the packaging material, for use in the treatment of an infection, as is further detailed hereinbelow.

The efficacy of the compositions described herein as disinfectants and in treating wounds is well demonstrated in the Examples section that follows.

Accordingly, according to an additional aspect of embodiments of the invention there is provided a kit, which comprises the antiseptic composition described herein, being packaged in a packaging material.

The kit can be labeled, for example, by being identified in print, in or on the packaging material, for use for disinfection purposes and/or for treating wounds, as detailed herein.

The components of the antiseptic composition can be packaged within the kit either together, as a single composition, or at least one of the component can be packaged individually. When one or more components are packaged individually, the kit may further be supplied with instructions indicating the route of preparing an antiseptic composition ready for use. Such instructions can be, for example, in accordance with the process of preparing the antiseptic composition, as is described in detail hereinafter.

According to a further aspect of some embodiments of the present invention, there is provided a method of disinfecting a substrate, which is effected by applying an effective amount of the antiseptic composition described herein onto the substrate, thereby disinfecting the substrate.

As used herein throughout, the term "disinfecting" refers to reducing the load of microorganism(s) in or on the substrate, to decreasing the rate of microorganism(s) growth in or on the substrate, to inhibiting or preventing the growth of microorganism(s) in or on the substrate, and/or to eradicating microorganism(s) in or on the substrate.

The term "substrate" as used herein, refers to any structure, product or material which can undesirably support, harbor or promote the growth of a microorganism on a surface thereof. Non-limiting examples include medical devices, medical equipments, containers of medical and pharmaceutical products, packaging materials, industrial equipments and machines used in the pharmaceutical, medical, agricultural, nutraceutical and food industries, walls, buildings, warehouse, compartment, container or transport vehicle, a dye or a paint and any other materials and industrial compounds which require protection of their surfaces against microbial attacks, such as, for example, construction materials.

According to some embodiments, applying the antiseptic composition onto the substrate is effected by, for example, washing the substrate with the composition, spreading the composition onto the substrate's surface, spraying the composition onto the substrate, or dipping the substrate in the composition. The route of application depends, at least in part, on the composition's form.

According to some embodiments, the substrate is a bodily surface of a subject in need thereof.

As used herein, the term "subject" refers to any animal e.g., a mammal, including, but not limited to, humans, non-human primates, mammals, rodents, and any other animal, which is to be the recipient of a particular treatment. Typically, the terms "subject" and "patient" are used interchangeably herein in reference to a human subject.

According to some embodiments, the method is effected by topical application of the antiseptic composition onto the bodily surface. According to some embodiments, the bodily surface is skin, a skin tissue, a mucosal tissue or any other infected or potentially infected body area that can benefit from topical application.

Accordingly, an antiseptic composition as described herein can be utilized for disinfecting an infected area (e.g., an acute or chronic wound, as detailed hereinafter) or for preventing infections in areas that are at risk for being infected. The latter include, for example, surgical wounds, acute wounds, ulcers and the like, which are highly susceptible to infections by various microorganisms.

As discussed hereinabove, the antiseptic compositions described herein have demonstrated efficient bactericidal activity against various bacterial strains as well as efficient fungicidal activity against various fungal strains. Thus, the antiseptic compositions described herein can be utilized in the treatment of wounds where the reduction of the microbial load in the wound is therapeutically beneficial.

Thus, according to an aspect of some embodiments of the present invention, there is provided a method of treating a wound in a subject in need thereof, the method comprising applying an effective amount of the antiseptic composition described herein to the wound area, thereby treating the wound.

According to some embodiments, the method is effected by topically applying the antiseptic composition onto the wound area.

The term "wound" is used herein to be construed according to its broadest meaning so as to describe damaged or disturbed skin or mucosal area, whether or not containing devitalized or eschar tissue, and encompasses any type of wound, including, but not limited to, acute wounds, chronic wounds, surgery wounds, burns and the like. The term "skin lesion" as used herein describes damaged skin and is used interchangeably with the term "wound" throughout the application.

The term "wound area" describes the area adjacent to the wound. This area typically extends from immediately adjacent the wound up to about 30 cm. It is being understood that the inner boundary of the area peripheral to the wound may conform to or parallel the shape of the wound.

The term "acute wound" describes a wound caused by a traumatic abrasion, laceration or through superficial damage, and which eventually heals spontaneously without complications through normal phases of wound healing (such as hemostasis, inflammation, proliferation and remodeling). Acute wounds, however, can often be complicated if become in contact with pathogenic microorganisms that may lead to local infection.

The phrases "surgery wound" and "surgical wound", which are used herein interchangeably, describe a wound that is formed as a result of a surgical procedure. Surgical wound infections are common, being 12% of all hospital-acquired infections. The rate of infection varies depending on the type of surgery undertaken. Especially high rates are associated with contaminated surgery, such as colorectal surgery or delayed surgery to traumatic wounds. Surgical wound infections are usually caused by the patient's normal flora or by bacteria from the environment or the skin of hospital staff. The most common microorganism that leads to surgical would infection is *Staphylococcus aureus*. Other common causative microorganisms include other Gram-negative aerobes, *Streptococcus* spp. and anaerobes.

The term "burns" describes wounds caused by heat, cold, electricity, chemicals, light, radiation, or friction. Burns can be highly variable in terms of the tissue affected, the severity, and resultant complications. Muscle, bone, blood vessel, and epidermal tissue can all be damaged with subsequent pain due to profound injury to nerve endings. Depending on the location affected and the degree of severity, a burn victim may experience a wide number of potentially fatal complications including shock, infection, electrolyte imbalance and respiratory distress. Infection is the most common complication of burns and is the major cause of death in burn victims. More than 10,000 Americans die every year from infectious complications of burns. Pathogenic microorganisms that commonly infect burn wounds include, for example, gram-positive bacteria such as methicillin-resistant *Staphylococcus aureus* (MRSA) and gram-negative bacteria such as *Acinetobacter baumannii-calcoaceticus* complex, *Pseudomonas aeruginosa*, and *Klebsiella* species.

The phrase "chronic wound" describes a wound in which there is no clot formation, normally occurring in patients who are compromised in some fashion and are less likely to heal. Examples of chronic wounds are chronic cutaneous ulcers such as diabetic ulcers, decubitus ulcers (pressure ulcers), and venous ulcers.

The phrase "diabetic ulcers" describes a wound caused by combination of factors associated with diabetes, such as decreased circulation, loss of sensation, structural foot deformities and loss of skin integrity. A diabetic ulcer can be a simple break in the skin, which does not heal in a timely and orderly fashion, or a wound that extends to deep structures and bone. Diabetic ulcers are often the entry points for bacteria and fungal organisms to invade the body, and the cause of limb and life threatening infection, often referred to in the art as diabetic infection. Diabetic infections are usually polymicrobial involving infections caused by multiple aerobic and anaerobic microorganisms. *Staphylococcus aureus*, beta-hemolytic *streptococcus*, Enterobacteriaceae, *Bacteroides fragilis, Peptococcus*, and *Peptostreptococcus* are exemplary strains that were cultured from diabetic ulcers.

The phrase "decubitus ulcers", also known as "pressure ulcers", describe skin lesions caused by variable factors such as: unrelieved pressure; friction; humidity; shearing forces; temperature; age; continence and medication; to any part of the body, especially portions over bony or cartilaginous areas such as sacrum, elbows, knees, ankles etc. Although easily prevented and completely treatable if found early, decubitus ulcers are often fatal and are one of the leading iatrogenic causes of death reported in developed countries. Decubitus ulcers may be caused by inadequate blood supply and resulting reperfusion injury when blood re-enters tissue. The most common organisms isolated from pressure ulcers are *Proteus mirabilis*, group D streptococci, *Escherichia coli, Staphylococcus species, Pseudomonas* species, and *Corynebacterium* organisms.

The phrase "venous ulcer" describes wounds that are thought to occur due to improper functioning of valves in the veins, usually of the legs, causing the pressure in the veins to increase. They are a major cause of chronic wounds, occurring in approximately 30-40% of chronic wound cases. Most venous ulcers are heavily contaminated with bacteria such as *Staphylococcus, Eschrichia coli, Proteus* and *Pseudomonas*.

As discussed hereinabove, reduction of the bacteria cell load in acute wounds and chronic wounds such as diabetic ulcers, decubitus ulcers (pressure ulcers), venous ulcer as well as burns by the antiseptic compositions described herein is therapeutically beneficial.

As further discussed hereinabove, the antiseptic compositions described herein have been found to effectively inhibit the growth of various bacterial strains. For example, a solution of 0.01% silver ions and 0.05% menthol, a composition according to some embodiments of the present invention, has been shown to efficiently kill upon contact and prevent growth of the bacterial strains *Escherichia coli* ATCC 47076, *Klebsiella pneumoniae*, a Methicillin Resistant clinical strain of *Staphylococcus aureus* (MRSA), a clinical strain of *Staphylococcus epidermis*, a clinical strain of Extended Spectrum β-lactamase producing *Escherichia coli*, a clinical strain of Multi Drug Resistant *Acinetobacter baumannii*, and a clinical strain of Multi Drug Resistant *Pseudomonas aeruginosa* (see, Tables 3 and 4). A solution of 0.01% silver ions and 0.05% menthol, a composition according to some embodiments of the present invention, has further been shown to exhibit fungicidal activity against *Trichophyton rubrum* clinical strain and *Microsporum canis* clinical strain (see, Example 6 hereinafter and FIGS. 2-4). Therefore, due to their broad antiseptic activity against various bacterial and fungal strains, including strains which are known to be isolated from wound areas, the antiseptic compositions described herein may be efficiently utilized in the treatment of wounds.

As further discussed herein and is demonstrated in the Examples section that follows, the antiseptic compositions described herein were shown to effectively inhibit microorganism's growth and to effectively prevent growth of various microorganisms in a non-sterile sample.

Accordingly, the antiseptic compositions described herein can be used in a method of treating or preventing an infection. The infection can be a bacterial infection, a fungal infection, an infection caused by a yeast, or any combination thereof.

The antifungal activity of the composition containing silver ions and menthol as described herein carries a vast therapeutic potential within the context of chronic diabetic foot ulcers as well as within the context of antifungal treatments of onychomycosis (fungal nail infections, mainly caused by the dermatophyte *Trichophyton rubrum*), dermatophytosis such as *Tinea pedis* (athlete's foot, also affected by *Trichophyton rubrum*) and *Tinea corporis* (dermatophyte skin invasion) and *Tinea capitis* (ringworm of the scalp and dermatophyte hair invasion) mainly affected by *Microsporum canis*.

There is a significant association between diabetes and occurrence of fungal foot infections: while in non-diabetic elderly population the incidence is 60%, in diabetic subjects the incidence rises to over 80%. Diabetes mellitus has a significant adverse effect on the occurrence of both *Tinea pedis* and onychomycosis, affecting x 1.48 increase ratio. Onychomycosis, often associated with *Tinea pedis*, substantially increase the risk of other infections, lesions formation eventually leading to chronic ulcers and amputations. The incidence of *Tinea pedis* in diabetic patients is 32% vs 7% in control population [Gupta A K, Humke S (2000) Eur J Dermatol 10: 379-384; Saunte et al. (2006) Acta Derm Venereol 86:425-428].

The term "disinfecting", as used herein throughout, thus encompasses treating an infection, as described herein.

In addition, the antiseptic compositions described herein can also be used as preservatives, for preventing or reducing formation of microbial load under non-sterile conditions and/or under conditions suspected as being adversely non-sterile.

The antiseptic compositions described herein can therefore be added, for example, to storage containers, particularly storage containers for storing and/or transporting medical products, such as medical devices, pharmaceutically active agents and drugs.

According to further aspects of embodiments of the invention, there is provided a use of the antiseptic composition described herein in the manufacture of a product for disinfecting a substrate, as described herein.

According to further aspects of embodiments of the invention, there is provided a use of the antiseptic composition described herein in the manufacture of a medicament for disinfecting a surface of a bodily area and/or for treating wounds, as described herein.

In any of the methods and uses described herein, the antiseptic compositions can be applied to the treated area using any suitable means.

Ordinarily, an absorbent of some type such as gauze, foam sponges, non-woven fabrics, cotton fabrics, cotton swabs or balls, and the like, are soaked with the composition and applied over the wound.

Alternatively, the composition can be in a form of a spray or aerosol, which can further comprise, for example, a film-forming agent. The composition is thus applied on the treated area by spraying.

Further alternatively, the composition can be in a form of a cream, a paste or a gel, and is applied onto the wound by spreading, or by applying an adhesive patch that comprises the composition.

Further alternatively and preferably, higher rates of wound healing can be achieved by applying the antiseptic composition over and through the wound in continuous flow so that the concentrations of the antiseptic agents and the hyperosmotic agent in contact with the wound are kept constant.

Accordingly, in some embodiments of the invention, the topical application of the antiseptic composition described herein is performed by streaming a flow of the antiseptic composition over and through the wound area.

The flow of the compositions described herein is conveyed over and through the wound for a predetermined period of time. According to some embodiments, conveying the flow continuously is performed for at least 5 minutes, in some embodiments for at least 15 minutes, in some embodiments for at least 30 minutes and in some embodiments for at least 1 hour. The wound is monitored for assessing the progress of reducing the microbial load and wound healing. A pause in the treatment for short periods of time can be carried out by arrest of the flow and removal of any conduits that prevent a free movement of the patient. An occlusive dressing to which the conduits are reattached may be left over the wound.

Treatment can be applied using an apparatus as described in U.S. Patent Application having Publication No. 2004/0186421 or WO2005/070480, which are incorporated by reference as if fully set forth herein.

According to an exemplary embodiment, such an apparatus comprises a housing having at least one aperture formed therein and means for affixing the apparatus to the skin around the circumference of the skin lesion, wherein the housing comprises (i) at least one inlet tube having a first longitudinal axis and configured to be adjustable along its longitudinal axis through the aperture; and (ii) at least one outlet tube having a second longitudinal axis.

The apparatus further comprises a reservoir adapted for holding the antiseptic composition, the reservoir being in fluid communication with the one or more inlets. An outlet may comprise valves for controlling the flow between the reservoir and the treatment zone. Preferably, an outlet may further comprise means enabling disconnecting and reconnecting the housing from the reservoir, thereby enabling to pause the treatment.

The simplicity of disconnecting and reconnecting the patient from the flow means enables applying the antiseptic compositions for prolonged periods of time. A flow of the antiseptic composition may last for at least one hour or may last for several hours, depending on individual needs.

According to some embodiments, the flow is induced by gravity from at least one reservoir that comprises the antiseptic composition.

According to some embodiments, the flow is induced by a pump being in fluid communication with at least one reservoir that comprises the antiseptic composition.

In some embodiments, the flow is induced by a peristaltic pump, which is not in direct contact with the streamed solution.

According to a further aspect of embodiments of the invention there is provided a process for preparing the antiseptic composition described herein, the process comprising mixing the source of silver ions, the menthol and the pharmaceutically acceptable carrier, so as to obtain the antiseptic composition.

According to some embodiments, the process further comprises admixing a hyperosmotic agent with the composition.

The order of addition of the composition components (i.e. source of silver ions, menthol, a pharmaceutically acceptable carrier and optionally a hyperosmotic agent) may vary, depending, for example, on solubilization considerations.

Thus, for example, the process can be effected by preparing a solution of a source of silver ions and carrier, and adding thereto menthol. Alternatively, the process can be effected by preparing a solution of menthol and a carrier and adding thereto the source of silver ions.

The hyperosmotic agent, if present, can be added before or after the addition of any of the silver ions or the menthol. Similarly, any other ingredients that are added to the composition, as described hereinabove, can be added at any stage.

According to some embodiments the process further comprises admixing said menthol with a solubilizing agent such as TWEEN 20, as described herein, to thereby obtain a solution of menthol and the solubilizing agent; and admixing said solution of menthol with the composition.

In some embodiments, the solubilizing agent is TWEEN 20. In some embodiments, the weight ratio between the menthol and the TWEEN 20 is 1:10. In some embodiments, the TWEEN 20 is utilized at a concentration of 0.5% w/v based on the total volume of the menthol and TWEEN 20 solution.

In some embodiments, the amounts of the source of silver ions and the menthol are such that upon mixing, the final concentration of the silver ions is from 0.05 mM to 30 mM, and the menthol final concentration is from 0.3 mM to 32 mM w. In some embodiments, the final concentration of the source of silver ions is from 0.3 mM to 0.6 mM, and the menthol final concentration is from 0.6 mM to 6.4 mM.

Considering the synergistic effect exhibited by combining menthol and a source of silver ions, which allows using a substantially reduced concentration of silver ions, as compared to currently available antiseptic products, according to a further aspect of embodiments of the invention there is provided a method of reducing a concentration of silver ions in an antiseptic composition which comprises silver ions (as an active ingredient). The method, according to these embodiments, is effected by admixing with a source of silver ions, a synergistically effective amount of menthol.

In some embodiments, the concentration of the silver ions is reduced by at least 2-folds, at least 3-folds, at least 5 folds, at least 6 folds, at least 7-folds, at least 8-folds, at least 9-folds, and even by an order of magnitude, and even twice thereof, or by 30-folds, 40 folds, 50-folds, 60-folds, 70-folds, 80-folds, 90-folds and 100-folds, as compared to an antiseptic composition that is devoid of a synergistically effective amount of menthol.

In some embodiments, the concentration of the silver ions is reduced by a 50-folds, as compared to an antiseptic composition that is devoid of a synergistically effective amount of menthol.

The phrase "antiseptic effective amount" describes the amount of an agent, herein, a source of silver ions, which exhibits an antiseptic activity, as defined herein.

The phrase "synergistically effective amount" describes a concentration of menthol upon being admixed with the source of silver ions in the antiseptic composition, which results in a synergistic effect of the combination of silver ions and menthol, as defined herein.

Further according to embodiments of the invention, there is provided a method of increasing an antiseptic activity of an antiseptic composition which comprises a source of silver ions at a concentration that is lower than 6 mM, the method being effected by admixing with the antiseptic composition a synergistically effective amount of menthol.

Admixing menthol with the antiseptic composition can be effected in accordance with the process of preparing an antiseptic composition, as described herein. Accordingly, additional components, such as a hyperosmotic agent, and a solubilizing agent, can also be admixed with the silver ions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental [support in the following examples.

EXAMPLES

Reference is now made to the following examples, which together with the above descriptions illustrate some embodiments of the invention in a non limiting fashion.

Materials and Experimental Methods

Materials:

LB medium was prepared by dissolving 10 grams Tryptone (Cat. No. 161200, Pronadisa, Conda), 5 grams yeast extract (Cat. No. 212750, DIFCO), 10 grams NaCl (Cat. No. 1.06404.1000, Merck) and 2 grams glucose (Cat. No. 1.08337.1000, Merck) in a final volume of 1 liter of highly purified water with magnetic stirring and mild heating. LB-agar was prepared by the addition of 15 grams of Bacto agar (Cat. No. 214010, BD) to LB medium.

BHI growth medium was obtained from Laboratory of Molecular Epidemiology and Antimicrobial Resistance, Tel Aviv Sourasky Medical Center.

$NaNO_3$ was obtained from Riedel-deHaën (Cat. No. 31440).

TWEEN 20 (Cat. No. 8.17072.1000), $AgNO_3$ (Cat. No. 1.01510.0050), Menthol (Cat. No. 1.05995.1000) Glycerol (Cat. No. 1.04093.1000), Tris (Cat. No. 1.08386.1000) and acetic acid glacial (Cat. No. 1.00056.2500) were obtained from Merck.

Compositions:

Silver nitrate and menthol solutions were prepared by adding final concentrations of 10% glycerol (hyperosmotic agent), menthol (0.5% TWEEN-20) and silver nitrate to a 50 mM Tris-buffer solution. The final composition was tittered to pH 7.45 using acetic acid glacial and then filtered through a 0.22 μm PES membrane filter. The sterile solutions thus obtained were clear and devoid of participates.

General Protocols:

E. Coli Growth Protocol:

A frozen stock of E. coli ATCC 47076 was grown overnight (1 ml in 9 ml LB medium) in a shaker incubator (200 rpm at 37° C.) until the $OD_{600nm}$ of the medium reached 1.6-1.8. One-ml aliquots of the culture medium were then transferred into 50 ml of fresh sterile LB medium and placed in a shaker incubator (200 rpm at 37° C.) for two hours until the $OD_{600nm}$ of the medium reached 0.6-0.8 ($2 \times 10^8$ colony forming unites per ml (CFU/ml)). The Bacterial suspension was adjusted to $10^8$ CFU/ml by dilution with sterile medium.

The Bacterial cells were then washed three times with 0.9% NaNO₃. The NaNo₃ washing cycles was performed by transferring 5 ml of the bacterial suspensions into 15 ml test tubes and subjecting the suspension to centrifugation at 4000 rpm at 4° C. for 5 minutes, followed by removal of the supernatant and re-suspension of the bacterial cell pellet in 5 ml of 0.9% NaNO₃.

The bactericidal activity of various concentration combinations of silver ions (from AgNO₃) and menthol (solubilized by the addition of 0.5% TWEEN 20) was then assessed by adding 5 ml of the tested combinations to the bacterial cell pellets prepared as described hereinbelow and re-suspending the cell pellets by vortex. A test tube containing only 0.9% NaNO₃ served as control.

The bacterial suspensions thus obtained were transferred to sterile glass tubes to reduce potential cell adsorption to the walls, and kept covered at 37° C. throughout the testing period. Following 5 minutes of static incubation, 100 µl samples of the treated bacterial suspension were removed, and 10 µl of decimal dilutions in NaNO₃ 0.9% of the suspension were dropped onto LB agar plates. The level of bacterial proliferation was assessed by counting the number of colonies that grew on the plates and calculating the CFU/ml and $\log_{10}$ CFU/ml following 18 hours of incubation at 37° C. Higher $\log_{10}$ CFU/ml calculated for a bacterial suspension, incubated with a specific combination, is indicative of a lower level of bactericidal activity of that combination.

Growth Protocol of Other Bacteria Cell Lines:

Various bacterial cells lines were obtained from the clinical strains collection of the Laboratory of Molecular Epidemiology and Antimicrobial Resistance, Tel Aviv Sourasky Medical Center. The bactericidal activity of the tested antiseptic combinations was thus tested against *Klebsiella pneumoniae*, a Methicillin Resistant clinical strain of *Staphylococcus aureus* (MRSA), a clinical strain of *Staphylococcus epidermis*, a clinical strain of Extended Spectrum β-lactamase producing *Escherichia coli*, a clinical strain of Multi Drug Resistant *Acinetobacter baumannii*, and a clinical strain of Multi Drug Resistant *Pseudomonas aeruginosa*.

The bacterial growth protocol was essentially as described above only that bacteria cell lines were grown in BHI growth medium (and following the growth of the cells in the medium, the bacterial suspension was adjusted to $10^7$ CFU/ml by dilution with sterile medium). In addition, in these experiments, the static incubation of each bacterial suspension with the silver ion+menthol combination was for 0, 30 and 60 minutes.

Synergy:

To asses whether menthol and silver ions act synergistically, the bactericidal activity observed when menthol and silver ions were administered together was compared to the bactericidal activity observed when each of these compounds was administered alone (determined after Lehmann, 2000. *Synergism in Disinfectant Formulation*, in *Disinfection, Sterilization, and Preservation* 5th ed., S. S. Block, Editor. Lippincott Williams and Wilkins. pp. 459-472).

A combination was considered synergistic when:

The bactericidal activity of menthol and silver ions was larger than the additive value of the bactericidal activity observed when each compound was tested, at the specific concentration, alone; or The time, until a certain level of bactericidal activity of menthol and silver ions was detected, was shorter than the time measured when each agent was tested, at the specific concentration, alone.

Example 1

Synergism of Bactericidal Activity of Menthol and Silver Ions in a Hyperosmotic Solution of 10% (v/v) Glycerol on *E. coli* ATCC 47076

For evaluation of synergy in bactericidal activity between menthol and silver ions, various concentration combinations of silver ions and menthol were used, as detailed in Table 1.

The results are summarized in Table 1 and show that synergy was observed for silver ions (derived from AgNO₃) and menthol combinations of 0.005% (w/v)+0.1% (w/v), 0.005%+0.05%, 0.0075%+0.05%, 0.01%+0.05% and 0.01%+0.01% w/v concentrations, respectively (corresponding to the shadowed areas in Table 1). These concentrations correspond to silver ions and menthol combinations at the following combinations: 0.29 mM+6.4 mM, 0.29 mM+3.2 mM, 0.44 mM+3.2 mM, 0.6 mM+3.2 mM and 0.6 mM+0.64 mM.

The left part of Table 1 presents the observed percentage of bacterial cells killed by each combination whereas the right part of Table 1 presents the expected percentage of bacterial cells killed if the bactericidal activity of menthol and silver ions were additive in nature rather than synergistic.

TABLE 1

| | % AgNO₃ | | | | | | | |
|---|---|---|---|---|---|---|---|---|
| | Measured values[a] | | | | Calculated accumulative values[b] | | | |
| | 0.01 | 0.0075 | 0.005 | 0 | 0.01 | 0.0075 | 0.005 | 0 |
| 0.1 | 100 | 100 | 100 | 51 | 112 | 115 | 66 | 51 |
| 0.05 | 100 | 100 | 100 | 20 | 81 | 84 | 35 | 20 |
| 0.01 | 100 | 56 | 48 | 0 | 61 | 64 | 15 | 0 |
| 0 | 61 | 64 | 15 | 0 | 61 | 64 | 15 | 0 |

[a]percentage of *E. Coli* cells killed by exposure to the indicated combination of menthol and AgNO₃.
[b]expected percentage of *E. Coli* cells killed, by the indicated combination when assuming an additive rather than synergistic activity between menthol and silver ions.

The synergistic combination of 0.01% silver ions and 0.05% menthol was selected for further studies.

Example 2

Bactericidal Activity of a Combination of 0.01% (w/v) Silver Ions and 0.05% (w/v) Menthol in a Hyperosmotic Solution Containing 10% (v/v) Glycerol on Various Types of Bacteria The effect of a combination of 0.01% silver ions and 0.05% menthol (solubilized by 0.5% (v/v) TWEEN 20) on the growth and viability of various types of bacteria was evaluated.

Cells incubated with NaNO₃ 0.9% (w/v) solution alone, without the addition of any antiseptic agent, served as control.

Bactericidal activity was defined as a 5-$\log_{10}$ or lower reduction in colony count as compared to control (after Cremieux, *Methods of testing Disinfectants*, in *Disinfection, Sterilization, and Preservation* 5th ed., S. S. Block, Editor. 2000, Lippincott Williams and Wilkins, pp 1305-1328.

Table 2 presents the $\log_{10}$ CFU/ml calculated for different types of bacterial cell suspensions incubated for 0, 30 and 60 minutes with no antiseptic agent (control) or either 0.01% silver ions (0.01% AgNO₃) alone, 0.05% menthol alone or a combination of 0.01% silver ions and 0.05% menthol. A baseline level was defined as the observed bacteria growth at time 0 when no antiseptic agent was added to the bacterial suspension.

The results clearly demonstrate the complete eradication of bacteria viability upon incubation of the bacterial suspension with the combination of 0.01% silver ions and 0.05% menthol. The effect was evident immediately (at time point 0) with the only exception being in the case of a Methicillin Resistant clinical strain of *Staphylococcus aureus* in which case an immediate 50% reduction in viability was observed followed by the killing of all bacteria after 30 minutes.

TABLE 2

| Bacteria | Baseline | Control[a] | | | 0.01% AgNO$_3$[a] | | | 0.05% Menthol[a] | | | 0.01% AgNO$_3$ and 0.05% Menthol[a] | | |
|---|---|---|---|---|---|---|---|---|---|---|---|---|---|
| | | 0 | 30 | 60 | 0 | 30 | 60 | 0 | 30 | 60 | 0 | 30 | 60 |
| *Escherichia coli* ATCC 47076 | 7.3 | 7.3 | 7.3 | 7.3 | 6.4 | 0 | 0 | 5.3 | 0 | 0 | 0 | 0 | 0 |
| *Klebsiella pneumoniae* | 6.8 | 6.8 | 6.7 | 6.5 | 0 | 0 | 0 | 6.2 | 4.9 | 3.8 | 0 | 0 | 0 |
| *Staphylococcus aureus* | 6.1 | 6.1 | 6.1 | 6.1 | 5.4 | 0 | 0 | 6.3 | 6.3 | 6.2 | 3.4 | 0 | 0 |
| *Staphylococcus epidermis* | 5.4 | 5.4 | 5.3 | 5.2 | 0 | 0 | 0 | 5.4 | 5.4 | 5.3 | 0 | 0 | 0 |
| beta-lactamase producing *Escherichia coli* | 5.9 | 5.9 | 5.8 | 5.6 | 4.8 | 0 | 0 | 4.9 | 4.9 | 4.9 | 0 | 0 | 0 |
| *Acinetobacter baumannii* | 6.4 | 6.4 | 6.4 | 6.4 | 6.3 | 0 | 0 | 6.4 | 6.3 | 6.2 | 0 | 0 | 0 |
| *Pseudomonas aeruginosa* | 6.5 | 6.5 | 6.5 | 7.1 | 5.1 | 0 | 0 | 5.8 | 3.5 | 2.5 | 0 | 0 | 0 |

[a] $\log_{10}$ CFU/ml of bacteria when the bacterial suspensions were treated with the indicated treatment for 0, 30 and 60 minutes.

These results point to a synergistic bactericidal activity exhibited by combining silver ions and menthol.

Example 3

Determination of the Minimum Inhibitory Concentration (MIC) and the Minimum Bactericidal Concentration (MBC) of a Combination of 0.01% (w/v) Silver Ions and 0.05% (w/v) Menthol General:

Studies were conducted for determining the effective use dilution of the tested silver ions-menthol combination against the test organism(s) using a tube dilution method. Serial dilutions were made of the tested sample in bacterial growth media. The test organisms were added to the product dilutions and incubated for growth. The dilutions of the tested sample that demonstrated no visible growth of the test organism were plated to confirm lethality of the product. This procedure is a standard susceptibility assay for antimicrobials and incorporates the intent of the American Society for Mocrobiology (ASM) methodology. Neutralization was confirmed at ≥70%.

Tested Sample:

The tested sample used was taken from a 250 ml Stock solution containing 0.1 mg silver nitrate per 1 ml buffered solution. Each tested sample contained the following components:

Glycerol: 10% v/v
Menthol: 0.05% w/v
TWEEN 20: 0.5% v/v
AgNO$_3$: 0.01% w/v
Tris: 50 mM Test Organisms:

The following microbial strains were used in this study:

*E. Coli* ATCC No. 8739; *Staphylococcus epidermidis* ATCC No. 12228; *Klebsiella pneumoniae* ATCC No. 4352; and *Staphylococcus aureus* ATCC No. 6538

Study Protocol:

Acceptance criteria: All positive controls should demonstrate growth of the target organism. All media and negative controls should demonstrate no growth of the target organism.

Culture Preparation Tubes of soybean casein digest broth (SCDB) were inoculated with stock cultures of bacteria and incubated at 37±2° C. for 18-48 hours. Where necessary, culture concentrations were adjusted by dilution in 0.9% sodium nitrate (NaNO$_3$) to approximately $10^8$ colony forming units (CFU)/ml using visual turbidity. On the day of testing, a standard plate count was performed on the suspension through dilution in 0.9% NaNO$_3$ and plating in triplicate on neutralizer agar (NUAG) to determine the starting titer.

MIC test procedure: The tested sample described hereinabove was two-fold serially diluted in sterile purified water (PURW). Next, 5 ml of each dilution was added to 5 ml of 2× media. The final test dilutions ranged from 1:2 to 1:4096.

Two positive control tubes, per organism, were prepared by mixing 5 ml PURW with 5 ml of 2× media. Two negative control tubes, per sample, were prepared by mixing 5 ml of the lowest sample dilution with 5 ml of 2× media. Two media control tubes were prepared by mixing 5 ml PURW with 5 ml of 2× media. No test culture was added to either negative control or media control tubes.

All test sample dilution and positive control tubes were inoculated with 0.05 ml of the test organism. All tubes were incubated at 37±2° C. for 16-20 hours. Based upon growth, each tube dilution was scored as either positive (+) or negative (0).

MBC test procedure: Dilutions demonstrating no growth were tested for MBC. A 0.1 ml aliquot was removed from each tube demonstrating no growth. Each dilution was plated in triplicate on NUAG. For a negative control, sterile 2× media were plated onto NUAG. Positive Controls were made by plating ≤100 CFU of the test organisms on NUAG. The test plates were incubated at 37±2° C. for 2-4 days.

Neutralization Verification:

The lowest dilution of the tested sample tested that inhibited growth of the tests organism (MIC) was tested for neutralization recovery of the test organism in 2× media. 0.1 ml aliquots of the tested sample dilution were plated in triplicate on NUAG. Three additional plates were prepared for each organism as a titer control. Plates were spiked with ≤100 CFU of the test organism. The plates were incubated at 37±2° C. for 2-4 days. The counts obtained from the titer control were compared to those of the test samples.

Results:

The results for the MIC and MBC are presented in Table 3. Table 4 presents the neutralization results.

Testing met the acceptance criteria stated above.

TABLE 3

| Test organism | MIC | Titer | MBC |
|---|---|---|---|
| *Escherichia coli* ATCC No. 8739 | 1:8 | $1.7 \times 10^8$ CFU/ml | 1:4 |
| *Staphylococcus epidermidis* ATCC No. 12228 | 1:8 | $5.7 \times 10^7$ CFU/ml | ND |
| *Klebsiella pneumoniae* ATCC No. 4352 | 1:8 | $1.3 \times 10^8$ CFU/ml | 1:4 |
| *Staphylococcus aureus* ATCC No. 6538 | 1:4 | $1.4 \times 10^8$ CFU/ml | ND |

TABLE 4

| Sample Dilution | Organism Identification | Percent Neutralization Recovery |
|---|---|---|
| 1:2 | *Escherichia coli* ATCC No. 8739 | 83 |
| 1:2 | *Staphylococcus epidermidis* ATCC No. 12228 | 117 |
| 1:2 | *Klebsiella pneumoniae* ATCC No. 4352 | 117 |
| 1:2 | *Staphylococcus aureus* ATCC No. 6538 | 100 |

These results provide further support for the versatile efficacious antimicrobial activity of the compositions described herein.

Example 4

Determination of USP Microbial Limit

Studies were conducted in order to determine the presence of *Staphylococcus aureus, Escherichia coli, Pseudomonas aeruginosa, Salmonella* sp. and other related organisms that may be objectionable or considered pathogenic in a non-sterile sample. The presence of these organisms indicates an environment that allows growth of similar pathogenic bacteria.

Study Protocol:

Acceptance Criteria: Raw plate count results should be within 30-300 colony forming units (CFU) per plate or reported as an estimate. *Aspergillus niger* and other similar organisms can accurately be read with only 8-80 CFU per plate. If no colonies are found, the results are reported as less than the sample dilution. The plate count is valid when the negative monitors are within the parameters established in the current procedure. Positive controls for qualification should demonstrate characteristic growth. Negative test monitors for the selective screening should not demonstrate growth of the indicator organism.

Sample Preparation: The tested sample was prepared by combining 10 ml of the sample stock solution as described in Example 3 hereinabove with 90 ml of 50 mM Tris-buffer pH 7.45. Ten-ml aliquots of this solution were then placed in 90 ml of fluid casein digest-soy lecithin-polysorbate 20 medium (FCDM) and acumedia lactose broth (ALBR).

Plate Counts: Using the pour plate technique, 1 ml of the sample was plated in soybean casein digest agar (SCDA) in triplicate for bacterial counts. The same procedure was performed using potato dextrose agar (PDXA) in triplicate for fungal counts. The SCDA plates were incubated for 48-72 hours at 30-35° C. while the PDXA plates were incubated for 5-7 days at 20-25° C.

Sample Enrichment: The samples were diluted in FCDM for *Staphylococcus aureus* and *Pseudomonas aeruginosa* screening, and ALBR for *Salmonella* and *Escherichia coli* screening.

The enrichment broths were allowed to incubate for 24-48 hours at 30-35° C.

Microbial Screening: Following enrichment incubation, the broths were transferred or streaked to the appropriate media for incubation as follows:

*Salmonella*: Selenite-cystine broth and Tetrathionate broth-12-24 hours at 30-35° C.; Brilliant green, Bismuth sulfite, and XLD agars—24-48 hours at 30-35° C.;

*P. aeruginosa*: Cetrimide agar—24-48 hours at 30-35° C.;

*S. aureus*: Mannitol salt agar—24-48 hours at 30-35° C.;

*E. coli*: MacConkey agar—24-48 hours at 30-35° C.

Any suspect colonies were verified using biochemical tests.

Qualification:

Qualification testing was performed on the initial test of this sample type as follows:

Twenty-four hour broth cultures of the four test organisms were grown at 30-35° C. and diluted 1:1000. The organism aliquot used for inoculation was ≤1% of the sample preparation. The inoculum was added within one hour of the dilution of the sample in the broths. The screening procedure was followed. All four test organisms must be recovered, demonstrating neutralization of the sample.

Results:

The tested solution passed qualification at the 1:10 dilution. Values observed for both the total aerobic microbial count and the combined mold and yeasts count were lower than 10, indicating "non detection".

Routine analysis may therefore be performed at the 1:10 sample dilution.

In the pathogenic screening, results showed that all tested organisms were absent from the total aerobic and fungal counts. The plate count results are not qualified for bacterial or fungal recovery.

Testing met the acceptance criteria.

Example 5

Anti-Microbial Susceptibility Test

Studies were conducted for screening a test sample containing silver ions and menthol for antimicrobial activity. The challenge organisms were *Staphylococcus aureus* ATCC No. 6538, and *Escherichia coli* ATCC No. 8739. The test procedure was an adaptation of the disk diffusion (Kirby-Bauer) method for antibiotic susceptibility testing.

Study Protocol:

Culture Preparation: Mueller-Hinton broth was inoculated with *S. aureus* and *E. coli* from stock cultures and incubated for 18-24 hours at 30-35° C. The test organisms were standardized using physiological saline to achieve a cell density equivalent to a McFatland Standard of 0.5. The inoculum was used within 15 minutes after standardization.

Tested Sample:

The tested sample used was taken from a 250 ml Stock solution containing 0.1 mg silver nitrate per 1 ml buffered solution. Each tested sample contained the following components:

Glycerol: 10% v/v
Menthol: 0.05% w/v
TWEEN 20: 0.5% v/v
$AgNO_3$: 0.01% w/v
Tris: 50 mM Test Performance: A sterile cotton swab was dipped into the standardized inoculum, rotated several times, and pressed firmly on the inside wall of the tube above the fluid level to remove excess inoculum from the swab. The swab was streaked over the entire surface of the Mueller-Hinton agar plate three times, with the plate rotated approximately 60° each time, then a final sweep was made around the agar rim. The lid was left agar for no longer than 15 minutes to allow any excess surface moisture to be absorbed. Sterile disks were placed on the agar plates using a pair of sterile forceps. One disk was placed in the center of each plate, pressing firmly so that the sample stayed in place and contacted the agar surface evenly. Each disk was inoculated with approximately 0.1 ml of the tested sample. For the negative controls, each disk was inoculated with sterile purified water.

The plates were incubated at 30-35° C. for approximately 24 hours. The samples were thereafter transferred to freshly prepared plates and incubated for approximately 24 hours. This procedure was repeated until plates showed no zone of inhibition. The diameters of the zones of inhibition (if present) were measured using calibrated calipers sensitive to 0.01 mm. The complete zone of inhibition, including the diameter of the sample, was measured.

Results:

The results are presented in Table 5, and demonstrate the susceptibility of the bacteria to the tested sample.

TABLE 5

| Test Organism | | Diameter of the zone including sample (mm) 24 hours | Diameter of the zone including sample (mm) 48 hours |
|---|---|---|---|
| Staphylococcus | 1 | 16.24 | No Zone |
| aureus ATCC No. | 2 | 16.34 | No Zone |
| 6538 | 3 | 15.33 | No Zone |
| Escherichia coli | 1 | 14.14 | No Zone |
| ATCC No. 8739 | 2 | 16.28 | No Zone |
| | 3 | 12.53 | No Zone |

Example 6

Comparative Study of Fungicidal/Fungistatic Activities of a Solution Containing Silver Ions and Menthol and of the Commercial B. Braun's PRONTOSAN The antifungal activity of the composition described herein (a tested sample as described in Example 5 hereinabove) was tested and compared to that of the commercially available products PRONTOSAN® (by B. Braun), MICROCYN® (by Occulus) and ANASEPT® (by Anacapa).

In Vitro Screening and Comparative Test of Fungicidal Activity:

SDB agar (100 µl) in ELISA plate well was inoculated with the tested strain, and was subjected to initial growth by incubation for 24 hours, at 30° C.

100 µl of an aqueous solution of the tested substance (either the solution containing silver ions and menthol, as described herein, or a solution of PRONTOSAN®, MICROCYN® or ANASEPT®, or of a 0.9% saline (as control), were applied once, plates were incubated for 30 minutes at 30° C., the solutions were discarded, and 100 µl of SDB growth medium was thereafter added, and plates were incubated for 30 minutes at 30° C. and then medium was discarded. Plates were then incubated at 30° C. for 24 days, and were examined and photographed daily.

FIG. 1 presents an image generally illustrating the appearance of a fungal culture following 24 days incubation after 30 minutes exposure to a tested solution and subsequent washing: there is either no growth (Fungicidal effect, denoted as "F"), minimal poor growth (Inhibitory effect, denoted as "IN") or full growth (No Effect, denoted "NE").

FIGS. 2-4 present images illustrating the appearance of the exposed fungal culture, following 3, 8, 11 and 16 days incubation after 30 minutes exposure to each of the tested solutions and subsequent washing. Tested solutions included: a composition containing silver ions and menthol as described in Example 5 hereinabove (denoted "S"), PRONTOSAN® (denoted "P"), alternating subsequent exposures to a composition containing silver ions and menthol (S) and PRONTOSAN® (P), (denoted "S+P" and "P+S"), MICROCYN® (denoted "M") and ANACEPT® (denoted "A") and their dilutions (1:2; 1:4; 1:8). Tested fungal strains were a clinical strain of *Trichophyton rubrum* (FIG. 2); *Trichophyton rubrum* NCPF 118 commercial strain (FIG. 3); and a clinical strain of *Microsporum canis* (FIG. 4).

The data presented in FIGS. 2-4 clearly demonstrate the fungicidal effect of a single treatment with the composition containing silver ions and menthol, according to embodiments of the invention. The silver ions-menthol composition exhibited an activity similar to that of PRONTOSAN®; was active also at 1:2-1:4 dilutions; and was superior to the hypochlorite-containing agents MICROCYN® and ANACEPT®. Furthermore, it was clearly demonstrated that subsequent treatments of the silver ions-menthol composition and PRONTOSAN® provided a substantially improved antifungal activity, with clear superiority of the order of the silver ions-menthol composition first and PRONTOSAN® next, which combination demonstrated significant high antifungal efficacy even at 1:8 dilutions on *Trichophyton rubrum* clinical strain (see, FIG. 2).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An antiseptic composition comprising, as active ingredients, menthol and silver ions, and a pharmaceutically acceptable carrier, wherein a concentration of said silver ions in said carrier is 0.6 mM, and a concentration of said menthol is 3.2 mM wherein said menthol and said silver ions act in synergy.

2. The antiseptic composition of claim 1, wherein a source of said silver ions is silver nitrate.

3. The antiseptic composition of claim 1, further comprising a hyperosmotic agent.

4. The antiseptic composition of claim 3, wherein said hyperosmotic agent is glycerol.

5. The antiseptic composition of claim 4, wherein a concentration of said glycerol is 10% v/v, based on the total volume of said antiseptic composition.

6. The antiseptic composition of claim 1, further comprising a solubilizing agent.

7. The antiseptic composition of claim 6, wherein said solubilizing agent is polyoxyethylene (20) sorbitan monolaurate.

8. The antiseptic composition of claim 1, wherein said pharmaceutically acceptable carrier is an aqueous solution.

9. The antiseptic composition of claim 1, being formulated as a topical dosage form.

10. The antiseptic composition of claim 9, wherein said topical dosage form is selected from the group consisting of a cream, a spray, a gauze, a wipe, a sponge, non-woven fabrics, a cotton fabrics, a foam, a solution, a lotion, an ointment, a paste and a gel.

11. An antiseptic kit comprising a packaging material and the antiseptic composition of claim 1 being packaged in said packaging material.

12. The antiseptic kit of claim 11, being identified in print, in or on said packaging material, for use in disinfecting a surface.

13. The antiseptic kit of claim 12, wherein said surface is a bodily surface.

14. The antiseptic kit of claim 11, being identified in print, in or on said packaging material, for use in the treatment of a wound.

15. The antiseptic kit of claim 14, wherein said wound is selected from the group consisting of an acute wound, a chronic wound, a burn and a surgical wound.

16. The antiseptic kit of claim 15, wherein said chronic wound is selected from the group consisting of a diabetic ulcer, a venous ulcer and a pressure ulcer.

17. A method of disinfecting a surface, the method comprising applying an effective amount of the antiseptic composition of claim 1 onto the surface, thereby disinfecting the surface.

18. The method of claim 17, wherein said surface is a bodily surface, the method being for disinfecting said bodily surface of a subject in need thereof.

19. The method of claim 18, comprising topically applying said antiseptic composition onto said bodily surface.

20. The method of claim 18, wherein said bodily surface is a skin tissue.

21. The method of claim 18, being for treating an infection in said bodily surface.

22. The method of claim 21, wherein said infection is caused by a pathogenic microorganism selected from the group consisting of bacteria, fungi and yeast.

23. A method of treating a wound in a subject in need thereof, the method comprising applying an effective amount of the antiseptic composition of claim 1 to the wound area, thereby treating the wound.

24. The method of claim 23, wherein the wound is selected from the group consisting of an acute wound, a chronic wound, a burn and a surgical wound.

25. The method of claim 24, wherein said chronic wound is selected from the group consisting of a diabetic ulcer, a venous ulcer and a pressure ulcer.

26. The method of claim 23, comprising topically applying said antiseptic composition onto said wound area.

27. The method of claim 26, wherein topically applying said antiseptic composition is performed by streaming a flow of the antiseptic composition over and through said wound area.

28. A process of preparing the antiseptic composition of claim 1, the process comprising admixing said silver ions, said menthol and said pharmaceutically acceptable carrier, thereby obtaining the antiseptic composition.

29. The process of claim 28, further comprising admixing a hyperosmotic agent with the composition.

30. The process of claim 28, further comprising admixing a solubilizing agent with the composition.

31. The process of claim 30, wherein said solubilizing agent is admixed with the menthol, prior to admixing the menthol with said silver ions and said carrier.

32. The process of claim 30, wherein said solubilizing agent is polyoxyethylene (20) sorbitan monolaurate.

* * * * *